US005631280A

United States Patent [19]
Ciccarone et al.

[11] Patent Number: 5,631,280
[45] Date of Patent: May 20, 1997

[54] INHIBITORS OF FARNESYL-PROTEIN TRANSFERASE

[75] Inventors: Terrence M. Ciccarone, Telford; Christopher J. Dinsmore, North Wales; Gerald E. Stokker, Gwynedd Valley; John S. Wai; Theresa M. Williams, both of Harleysville, all of Pa.

[73] Assignee: Merck & Co., Inc., Rahway, N.J.

[21] Appl. No.: 448,865

[22] Filed: May 24, 1995

Related U.S. Application Data

[63] Continuation-in-part of Ser. No. 412,621, Mar. 29, 1995, abandoned.

[51] Int. Cl.$^6$ .................... A61K 31/40; C07D 209/44
[52] U.S. Cl. ................... 514/416; 514/418; 514/576; 514/649; 548/472; 548/486; 564/162
[58] Field of Search ...................... 548/472, 486; 564/162; 514/416, 418, 576, 649

[56] References Cited

U.S. PATENT DOCUMENTS

| | | |
|---|---|---|
| 5,043,268 | 8/1991 | Stock . |
| 5,141,851 | 8/1992 | Brown et al. . |
| 5,238,922 | 8/1993 | Graham et al. . |
| 5,326,773 | 7/1994 | De Solms et al. . |
| 5,326,776 | 7/1994 | Winn et al. . |
| 5,340,828 | 8/1994 | Graham et al. . |
| 5,352,705 | 10/1994 | Deana et al. . |

FOREIGN PATENT DOCUMENTS

| | | |
|---|---|---|
| 0456180A1 | 11/1991 | European Pat. Off. . |
| WO91/16340 | 10/1991 | WIPO . |
| WO95/00493 | 1/1995 | WIPO . |
| WO95/11917 | 5/1995 | WIPO . |

OTHER PUBLICATIONS

Harrington, E.M. et al., Bioorganic and Medicinal Chemistry Letters, vol. 4, No. 23, pp. 2775–2780, 1994.
Nigam, M. et al., Journal of Biological Chemistry, vol. 268, No. 28, pp. 20695–20698, Oct., 1993.
Qian, Y., et al., Bioorganic and Medicinal Chemistry Letters, vol. 4, No. 21, pp. 2579–2584, 1994.
Gibbs, J.B. et al., "Selective Inhibition of Farnesyl–Protein Transferase Blocks Ras Processing in Vivo", The Journal of Biological Chemistry, vol. 268, No. 11, pp. 7617–7620 (1993).
Goldstein, J.L. et al., "Nonfarnesylated Tetrapeptide Inhibitors of Protein Farnesyltransferase", The Journal of Biological Chemistry, vol. 266, No. 24 pp. 15575–15578 (1991).
James, G.L. et al., "Benzodiazepine Peptidomimetic BZA–5B Interrupts the MAP Kinase Activation Pathway in H–Ras–transformed Rat–1 Cells, but Not in Untransformed Cells", The Journal of Biological Chemistry, vol. 369, No. 44, pp. 27705–27714 (1994).
James, G.L. et al., "Benzodiazepine Peptidomimetics: Potent Inhibitors of Ras Farnesylation in Animal Cells", Science, vol. 260, pp. 1937–1942 (1993).
James, G., et al., "Polylysine and CVIM Sequences of K–RasB Dictate Specificity of Prenylation and Confer Resistance to Benzodiazepine Peptidomimetic in Vitro", The Journal of Biological Chemistry, vol. 270, No. 11, pp. 6221–6226 (1995).
Kohl, N.E. et al., "Selective Inhibition of ras–Dependent Transformation by a Farnesyltransferase Inhibitor", Science, vol. 260, pp. 1934–1937 (1993).
Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).
Nigam, M., et al., "Potent Inhibition of Human Tumor p21 ras Farnesyltransferase by A1A2–lacking p21 ras CA1A2X Peptidomimetics", The Journal of Biol. Chem., vol. 268, Issue of Oct. 5, pp. 20695–20698 (1993).
Pompliano, D.L., "Steady–State Kinetic Mechanism of Ras Farnesyl:Protein Transferase", Biochemistry, vol. 31, pp. 3800–3807 (1992).
Qian, T., et al., "Design and Structural Requirements of Potent Peptidomimetic Inhibitors of p21 ras Farnesyltransferase", The Journal of Biol. Chem., vol. 269, No. 17, Issue of Apr. 29, pp. 12410–12413 (1994).
Vogt, A., et al. "A Non–peptide Mimetic of Ras–CAAX: Selective Inhibition of Farnesyltransferase and Ras Processing", The Journal of Biol. Chem., vol. 270, No. 2, Issue of Jan. 13, pp. 660–664 (1995).
Kohl, N.E., et al., "Inhibition of farnesyltransferase induces regression of mammary and salivary carcinomas in ras transgenic mice," Nature Medicine, vol. 1, No. 8, pp. 792–797 (1995).

*Primary Examiner*—Jacqueline Haley
*Attorney, Agent, or Firm*—David A. Muthard; Mark R. Daniel

[57] ABSTRACT

The present invention comprises peptidomimetic compounds which comprise a suitably aniline and aminoalkylbenzene moieties. The instant compounds inhibit the farnesyl-protein transferase enzyme and the farnesylation of certain proteins. The invention is further directed to chemotherapeutic compositions containing the compounds of this invention and methods for inhibiting farnesyl-protein transferase and the farnesylation of the oncogene protein Ras.

30 Claims, No Drawings

INHIBITORS OF FARNESYL-PROTEIN TRANSFERASE

RELATED APPLICATION

The present patent application is a continuation-in-part application of application Ser. No. 08/412,621, filed Mar. 29, 1995, now abandoned.

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. In the peptide derived class of inhibitors, a subclass of inhibitors has been described which generally comprises cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)).

Another subclass of the peptide derived inhibitors which comprises peptidomimetic compounds wherein the central AA portion of the CAAX motif has been replaced by 3-aminobenzoic acid and 3aminomethylbenzoic acid spacers has recently been described (M. Nigam et al. *J. Biol. Chem.*, 268:20695–20698 (1993), Y. Qian et al. *J. Biol. Chem.*, 269:12410–12413 (1994)). Those compounds, which incorporated a peptidyl moiety having a free carboxylic acid at the C-terminus, required development of a prodrug ester for in vivo efficacy. FPTase peptidomimetic inhibitors further lacking a C-terminus peptidyl moiety (wherein the X peptide has been replaced by a non-peptide moiety) have also been recently described (A. Vogt et al. J. Biol. Chem., 270:660–664 (1995)).

It is an object of this invention to develop non-peptide compounds which will inhibit farnesyl-protein transferase and the growth of cancer cells. It is a further object of this invention to develop chemotherapeutic compositions containing the compounds of this invention, and methods for producing the compounds of this invention.

SUMMARY OF THE INVENTION

The present invention includes substituted aniline and aminoalkylbenzene analogs which inhibit farnesyl-protein transferase and the farnesylation of the oncogene protein Ras, chemotherapeutic compositions containing the compounds of this invention, and methods for producing the compounds of this invention. The compounds of the instant invention lack a free carboxylic acid moiety at the C-terminus of the molecule, thereby avoiding the necessity of developing a prodrug strategy for inhibition in vivo.

The compounds of this invention are illustrated by the formulae A, B, C and D:

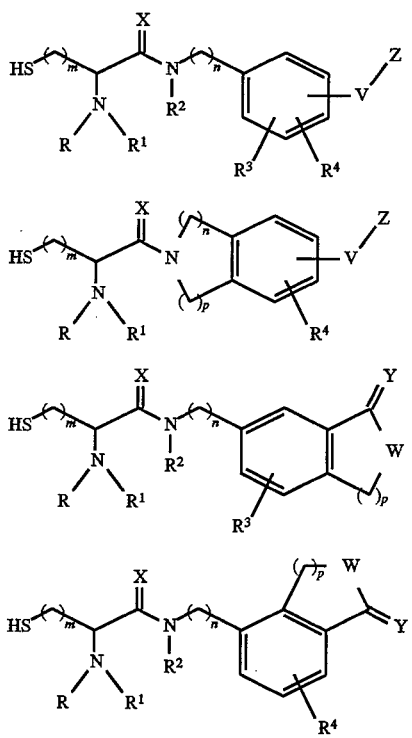

DETAILED DESCRIPTION OF THE INVENTION

The compounds of this invention are useful in the inhibition of farnesyl-protein transferase and the farnesylation of certain proteins. In a first embodiment of this invention, the inhibitors of farnesyl-protein transferase are illustrated by the formula A:

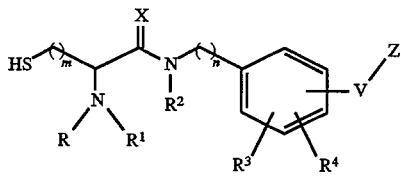

wherein:
X is O or $H_2$;
m is 1 or 2;
n is 0 or 1;
q is 0, 1 or 2;
t is 1 to 4;
$R, R^1$ and $R^2$ are independently selected from: H, $C_{1-6}$ alkyl, or $C_{1-6}$ aralkyl;
$R^3$ and $R^4$ are independently selected from:
  a) hydrogen,
  b) $C_1$–$C_6$ alkyl unsubstituted or substituted by $C_2$–$C_6$ alkenyl, $R^6O$—, $R^5S(O)_q$—, $R^7C(O)NR^6$—, CN, $N_3$, $R^6OC(O)NR^6$—, $R^6R^7N$—$C(NR^6R^8)$—, $R^6C(O)$—, $R^7R^8NC(O)O$—, $R^7R^8NC(O)$—, $R^6R^7N$—$S(O)_2$—, —$NR^6S(O)_2R^5$, $R^6OC(O)O$—, —$NR^6R^7$, or $R^7R^8NC(O)NR^6$—,
  c) unsubstituted or substituted cycloalkyl, alkenyl, $R^6O$—, $R^5S(O)_q$—, $R^6C(O)NR^6$—, CN, $NO_2$, $R^6R^7N$—$C(NR^8)$—, $R^6C(O)$—, $N_3$, —$NR^6R^7$, halogen or $R^7OC(O)NR^6$—, and
  d) $C_1$–$C_6$ alkyl substituted with an unsubstituted or substituted group selected from aryl, heterocyclic and $C_3$–$C_{10}$ cycloalkyl;

Z is unsubstituted or substituted $C_{1-8}$ alkyl, unsubstituted or substituted $C_{2-8}$ alkenyl, unsubstituted or substituted aryl, unsubstituted or substituted heterocycle;
wherein the substituted group is substituted with one or more of:
  1) $C_{1-4}$ alkyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
  2) aryl or heterocycle,
  3) halogen,
  4) $OR^6$,
  5) $NR^6R^7$,
  6) CN,
  7) $NO_2$, or
  9) $CF_3$;
$R^5$ is $C_{1-4}$ alkyl or aralkyl;
$R^6, R^7$ and $R^8$ are independently selected from: H, $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO, e) 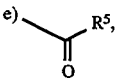

f) —$SO_2R^5$, or
  g) —$NR^6R^7$, or
$R^6$ and $R^7$ may be joined in a ring, and
$R^7$ and $R^8$ may be joined in a ring;
$R^9$ is selected from: H, $C_{1-4}$ alkyl, $C_{3-6}$ cycloalkyl, heterocycle and aryl, unsubstituted, monosubstituted or disubstituted with substituents independently selected from:
  a) $C_{1-4}$ alkyl,
  b) $C_{1-4}$ alkoxy,
  c) aryl or heterocycle,
  d) halogen,
  e) HO, f) 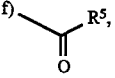

g) —$SO_2R^5$, and
  h) —$NR^6R^7$;
V is selected from: —$C(R^{11})$=$C(R^{11})$—, —C≡C—, —C(O)—, —$C(R^{11})_2$—, —$C(OR^{11})R^{11}$—, —$CN(R^{11})_2 R^{11}$—, —$OC(R^{11})_2$—, —$NR^{11}C(R^{11})_2$—, —$C(R^{11})_2 O$—, —$C(R^{11})_2 NR^{11}$—, —$C(O)NR^{11}$—, —$NR^{11}C(O)$—, $O$, —$NC(O)R^{11}$—, —$NC(O)OR^{11}$—, —$S(O)_2N(R^{11})$—, —$N(R^{11})S(O)_2$—, or $S(O)_m$;
$R^{10}$ and $R^{11}$ are independently selected from hydrogen, $C_1$–$C_6$ alkyl, $C_2$–$C_4$ alkenyl, benzyl and aryl;
or the disulfide or pharmaceutically acceptable salts thereof.

In a second embodiment of this invention, the inhibitors of farnesyl-protein transferase are illustrated by the formula B:

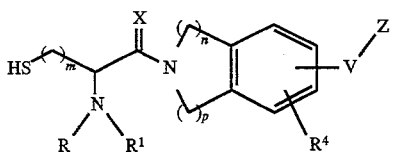 B wherein:

X is O or $H_2$;
m is 1 or 2;
n is 0 or 1;
p is 1, 2 or 3;
q is 0, 1 or 2;
t is 1 to 4;
R and $R^1$ are independently selected from: H, $C_{1-6}$ alkyl, or $C_{1-6}$ aralkyl;
$R^4$ is independently selected from:

a) hydrogen,
b) $C_1-C_6$ alkyl unsubstituted or substituted by $C_2-C_6$ alkenyl, $R^6O-$, $R^5S(O)_q-$, $R^7C(O)NR^6-$, CN, $N_3$, $R^6OC(O)NR^6-$, $R^6R^7N-C(NR^6R^8)-$, $R^6C(O)-$, $R^7R^8NC(O)O-$, $R^7R^8NC(O)-$, $R^6R^7N-S(O)_2-$, $-NR^6S(O)_2R^5$, $R^6OC(O)O-$, $-NR^6R^7$, or $R^7R^8NC(O)NR^6-$,
c) unsubstituted or substituted cycloalkyl, alkenyl, $R^6O-$, $R^5S(O)_q-$, $R^6C(O)NR^6-$, CN, $NO_2$, $R^6R^7N-C(NR^8)-$, $R^6C(O)-$, $N_3$, $-NR^6R^7$, halogen or $R^7OC(O)NR^6-$, and
d) $C_1-C_6$ alkyl substituted with an unsubstituted or substituted group selected from aryl, heterocyclic and $C_3-C_{10}$ cycloalkyl;

Z is unsubstituted or substituted $C_{1-8}$ alkyl, unsubstimted or substituted $C_{2-8}$ alkenyl, unsubstimted or substituted aryl or unsubstituted or substituted heterocycle;

wherein the substituted group is substituted with one or more of:

1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
2) aryl or heterocycle,
3) halogen,
4) $OR^6$,
5) $NR^6R^7$,
6) CN,
7) $NO_2$, or
9) $CF_3$;

$R^5$ is $C_{1-4}$ alkyl or aralkyl;
$R^6$, $R^7$ and $R^8$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:

a) $C_{1-4}$ alkoxy,
b) aryl or heterocycle,
c) halogen,
d) HO, e) 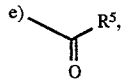

f) $-SO_2R^5$, or
g) $-NR^6R^7$, or $R^6$ and $R^7$ may be joined in a ring, and
$R^7$ and $R^8$ may be joined in a ring;

$R^9$ is selected from: H; $C_{1-4}$ alkyl, $C_{3-6}$ cycloalkyl, heterocycle and aryl, unsubstituted, monosubstituted or disubstituted with substituents independently selected from:

a) $C_{1-4}$ alkyl,
b) $C_{1-4}$ alkoxy,
c) aryl or heterocycle,
d) halogen,
e) HO, f) 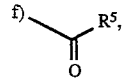

g) $-SO_2R^5$, and
h) $-NR^6R^7$;

V is selected from: $-CH=CH-$, $-C\equiv C-$, $-C(O)-$, $-C(R^{11})_2-$, $-C(OR^{11})R^{11}-$, $-CN(R^{11})_2R^{11}-$, $-OC(R^{11})_2-$, $-NR^{11}C(R^{11})_2-$, $-C(R^{11})_2O-$, $-C(R^{11})_2NR^{11}-$, $-C(O)NR^{11}-$, $-NR^{11}C(O)-$, O, $-NC(O)R^{11}-$, $-NC(O)OR^{11}-$, $-S(O)_2N(R^{11})-$, $-N(R^{11})S(O)_2-$, or $S(O)_m$;

$R^{10}$ and $R^{11}$ are independently selected from hydrogen, $C_1-C_6$ alkyl, $C_2-C_4$ alkenyl, benzyl and aryl;

or the disulfide or pharmaceutically acceptable salts thereof.

In a third embodiment of this invention, the inhibitors of farnesyl-protein transferase are illustrated by the formula C:

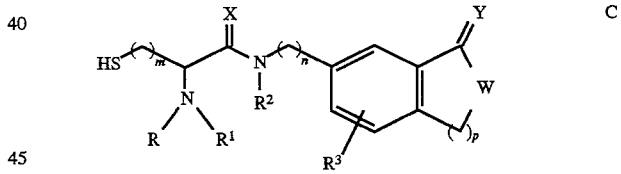 C wherein:
X and Y are independently O or $H_2$;
m is 1 or 2;
n is 0 or 1;
p is 1, 2 or 3;
q is 0, 1 or 2;
t is 1 to 4;
R, $R^1$ and $R^2$ are independently selected from: H, $C_{1-6}$ alkyl, or $C_{1-6}$ aralkyl;
$R^3$ is independently selected from:

a) hydrogen,
b) $C_1-C_6$ alkyl unsubstituted or substituted by $C_2-C_6$ alkenyl, $R^6O-$, $R^5S(O)_q-$, $R^7C(O)NR^6-$, CN, $N_3$, $R^6OC(O)NR^6-$, $R^6R^7N-C(NR^6R^8)-$, $R^6C(O)-$, $R^7R^8NC(O)O-$, $R^7R^8NC(O)-$, $R^6R^7N-S(O)_2-$, $-NR^6S(O)^2R^5$, $R^6OC(O)O-$, $-NR^6R^7$, or $R^7R^8NC(O)NR^6-$,
c) unsubstituted or substituted cycloalkyl, alkenyl, $R^6O-$, $R^7S(O)_q-$, $R^6C(O)NR^6-$, CN, $NO_2$, $R^6R^7N-C(NR^8)-$, $R^6C(O)-$, $N_3$, $-NR^6R^7$, halogen or $R^7OC(O)NR^6-$, and d) $C_1$–$C_6$ alkyl substituted with an unsubstituted or substituted group selected from aryl, heterocyclic and $C_3$–$C_{10}$ cycloalkyl;

W is —CHR$^9$— or —NR$^9$—;

R$^5$ is $C_{1-4}$ alkyl or aralkyl;

R$^6$, R$^7$ and R$^8$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO,
  e) 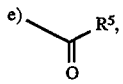
  f) —SO$_2$R$^5$, or
  g) —NR$^6$R$^7$, or R$^6$ and R$^7$ may be joined in a ring, and
R$^7$ and R$^8$ may be joined in a ring;

R$^9$ is selected from: H; $C_{1-4}$ alkyl, $C_{3-6}$ cycloalkyl, heterocycle and aryl, unsubstituted, monosubstituted or disubstituted with substituents independently selected from:
  a) $C_{1-4}$ alkyl,
  b) $C_{1-4}$ alkoxy,
  c) aryl or heterocycle,
  d) halogen,
  e) HO,
  f) 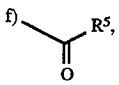
  g) —SO$_2$R$^5$, and
  h) —NR$^6$R$^7$;

or the disulfide or pharmaceutically acceptable salts thereof.

In a fourth embodiment of this invention, the inhibitors of farnesyl-protein transferase are illustrated by the formula D:

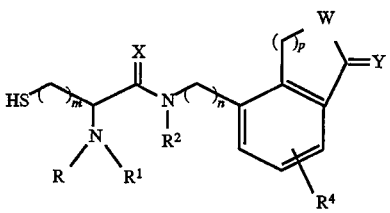

wherein:
X and Y are independently O or H$_2$;
m is 1 or 2;
n is 0 or 1;
p is 1, 2 or 3;
q is 0, 1 or 2;
t is 1 to 4;
R, R$^1$ and R$^2$ are independently selected from: H, $C_{1-6}$ alkyl, or $C_{1-6}$ aralkyl;
R$^4$ is independently selected from:
  a) hydrogen,
  b) $C_1$–$C_6$ alkyl unsubstituted or substituted by $C_2$–$C_6$ alkenyl, R$^6$O—, R$^5$S(O)$_q$—, R$^7$C(O)NR$^6$—, CN, N$_3$, R$^6$OC(O)NR$^6$—, R$^6$R$^7$N—C(NR$^6$R$^8$)—, R$^6$C(O)—, R$^7$R$^8$NC(O)O—, R$^7$R$^8$NC(O)—, R$^6$R$^7$N—S(O)$_2$—, —NR$^6$S(O)$_2$R$^5$, R$^6$OC(O)O—, —NR$^6$R$^7$, or R$^7$R$^8$NC(O)NR$^6$—, c) unsubstituted or substituted cycloalkyl, alkenyl, R$^6$O—, R$^5$S(O)$_q$—, R$^6$C(O)NR$^6$—, CN, NO$_2$, R$^6$R$^7$N—C(NR$^8$)—, R$^6$C(O)—, N$_3$, —NR$^6$R$^7$, halogen or R$^7$OC(O)NR$^6$—, and
  d) $C_1$–$C_6$ alkyl substituted with an unsubstituted or substituted group selected from aryl, heterocyclic and $C_3$–$C_{10}$ cycloalkyl;

W is —CHR$^9$— or —NR$^9$—;

R$^5$ is $C_{1-4}$ alkyl or aralkyl;

R$^6$, R$^7$ and R$^8$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO,
  e) 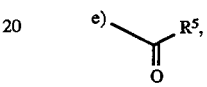
  f) —SO$_2$R$^5$, or
  g) —NR$^6$R$^7$, or R$^6$ and R$^7$ may be joined in a ring, and
R$^7$ and R$^8$ may be joined in a ring;

R$^9$ is selected from: H; $C_{1-4}$ Alkyl, $C_{3-6}$ cycloalkyl, heterocycle and aryl, unsubstituted, monosubstituted or disubstituted with substituents independently selected from:
  a) $C_{1-4}$ alkyl,
  b) $C_{1-4}$ alkoxy,
  c) aryl or heterocycle,
  d) halogen,
  e) HO,
  f) 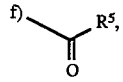
  g) —SO$_2$R$^5$, and
  h) —NR$^6$R$^7$;

or the disulfide or pharmaceutically acceptable salts thereof.

In a preferred embodiment of the instant invention, compounds of this invention are illustrated by the following formula:

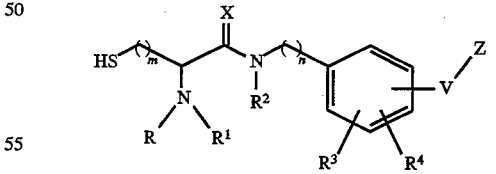

wherein:
X is H$_2$;
m is 1;
n is 0 or 1;
R, R$^1$ and R$^2$ are independently selected from: H, $C_{1-6}$ alkyl, or $C_{1-6}$ aralkyl;
R$^3$ and R$^4$ are independently selected from: H, $C_{1-8}$ alkyl, aryl, —SO$_2$R$^5$, —OR$^6$;
Z is unsubstituted or substituted $C_{1-8}$ alkyl, unsubstimted or substituted aryl or unsubstituted or substituted heterocycle;

wherein the substituted group is substituted with one or more of:

1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
2) aryl or heterocycle,
3) halogen,
4) $OR^6$,
5) $NR^6R^7$,
6) CN,
7) $NO_2$, or
9) $CF_3$;

$R^5$ is $C_{1-4}$ alkyl or aralkyl;

$R^6$ and $R^7$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstimted or substituted with:
   a) $C_{1-4}$ alkoxy,
   b) aryl or heterocycle,
   c) halogen,
   d) HO, e) $\overset{R^5}{\underset{O}{\|}}$, f) —$SO_2R^5$, or
g) —$NR^6R^7$, or $R^6$ and $R^7$ may be joined in a ring, and V is selected from: —CH=CH—, —C≡C—, —C(O)—, —C(R$^{11}$)$_2$—, —C(OR$^{11}$)R$^{11}$—, —CN(R$^{11}$)$_2$R$^{11}$—, —OC(R$^{11}$)$_2$—, —NR$^{11}$C(R$^{11}$)$_2$—, —C(R$^{11}$)$_2$O—, —C(R$^{11}$)$_2$NR$^{11}$—, —C(O)NR$^{11}$—, —NR$^{11}$C(O)—, O, —NC(O)R$^{11}$—, —NC(O)OR$^{11}$—, —S(O)$_2$N(R$^{11}$)—, —N(R$^{11}$)S(O)$_2$—, or S(O)$_m$;

$R^{10}$ and $R^{11}$ are independently selected from hydrogen, $C_1$–$C_6$ alkyl, $C_2$–$C_4$ alkenyl, benzyl and aryl;

or the disulfide or pharmaceutically acceptable salts thereof.

In a second preferred embodiment of this invention, the inhibitors of farnesyl-protein transferase are illustrated by the formula D:

![Structure D]

wherein:
X is $H_2$;
Y is O;
m is 1;
n is 0 or 1;
p is 1, 2 or 3;
t is 1 to 4;
R, $R^1$ and $R^2$ are independently selected from: H, $C_{1-6}$ alkyl, or $C_{1-6}$ aralkyl;
$R^4$ is selected from: H; $C_{1-8}$ alkyl, aryl, —$SO_2R^5$, —$OR^6$,
W is —$NR^9$—;
$R^5$ is $C_{1-4}$ alkyl or aralkyl;

$R^6$ and $R^7$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
   a) $C_{1-4}$ alkoxy,
   b) aryl or heterocycle,
   c) halogen,
   d) HO, e) $\overset{R^5}{\underset{O}{\|}}$, f) —$SO_2R^5$, or
g) —$NR^6R^7$, or $R^6$ and $R^7$ may be joined in a ring;

$R^9$ is selected from: H, $C_{1-4}$ alkyl and aryl, unsubstituted, monosubstituted or disubstituted with substituents independently selected from:
   a) $C_{1-4}$ alkyl,
   b) $C_{1-4}$ alkoxy,
   c) aryl or heterocycle,
   d) halogen,
   e) HO, f) $\overset{R^5}{\underset{O}{\|}}$, g) —$SO_2R^5$, and
h) —$NR^6R^7$;

or the disulfide or pharmaceutically acceptable salts thereof.

The preferred compounds of this invention are as follows:

3-[2(R)-Amino-3-mercaptopropylamino]-N-(2,3-dimethylphenyl)-benzamide

3-[2(R)-Amino-3-mercaptopropylamino]-N-phenyl-N-methylbenzamide

3-[2(R)-Amino-3-mercaptopropylamino]-N-(1-naphthylmethyl)-benzamide

3-[2(R)-Amino-3-mercaptopropylamino]-N-phenylbenzamide

3-[2(R)-Amino-3-mercaptopropylamino]-N-benzylbenzamide

3-[2(S)-Amino-3-mercaptopropylamino]-N-(2,3-dimethylphenyl)-benzamide

3-[2(R)-Amino-3-mercaptopropanoylamino]-N-(2,3-dimethylphenyl)-benzamide

3-[2(R)-Amino-3-mercaptopropylamino]-4-methyl-N-(2,3-dimethylphenyl)-benzamide

3-[2(R)-Amino-3-mercaptopropylamino]-4-methoxy-N-(2,3-dimethylphenyl)-benzamide

3-[2(R)-Amino-3-mercaptopropylamino]-6-methyl-N -(2,3-dimethylphenyl)-benzamide

3-[2(R)-Amino-3-mercaptopropylamino]-N-[1-(5,6,7,8-tetrahydronaphthyl)]-benzamide 1-[3-[2(R)-Amino-3-mercaptopropylamino]phenylcarbonyl]indoline 1-[2(R)-Amino-3-mercaptopropylamino]-3-[(2,3-dimethylbenzoyl)-amino]-benzene 4-[2(R)-Amino-3-mercaptopropylamino]-2-(2,3-dimethylphenyl)-isoindolin-1-one 4-[2(R)-Amino-3-mercaptopropylamino]-2-benzylisoindolin-1-one -1-[2(R)-Amino-3-mercaptopropylamino]-N-(2,3-dimethylphenyl)-4-indoline carboxamide 1-[2(R)-Amino-3-mercaptopropylamino]-3-[(2,3-dimethylphenyl)aminomethyl]-benzene 3-[2(R)-Amino-3-mercaptopropylaminomethyl]-N-(2,3-dimethylphenyl)-benzamide 3-[2(R)-Amino-3-mercaptopropylamino]benzophenone 3-[2(R)-Amino-3-mercaptopropylamino]-4-pentyl-N-(2,3-dimethylphenyl)-benzamide 3-[2(R)-Amino-3-mercaptopropylamino]-4-ethyl-N-(2,3-dimethylphenyl)-benzamide

[N-[(2R )-2-amino-3-mercaptopropyl]amino-3-[2-(3-methylphenyl)-trans-ethenyl]benzene N-[(2R)-2-amino-3-mercaptopropyl]amino-3-[(1-naphthylmethyl)oxy]benzene N-[(2R)-2-amino-3-mercaptopropyl]amino-2-(phenoxy) benzene N-[(2R)-2-amino-3-mercaptopropyl]amino-2-(benzyloxy) benzene N-[(2R)-2-amino-3-mercaptopropyl]amino-4-(phenoxy) benzene N-[(2R)-2-amino-3-mercaptopropyl]amino-4-[(3-methylphenyl)oxy]benzene N-[(2R)-2-amino-3-mercaptopropyl]amino-3-(phenoxy) benzene N-[(2R)-2-amino-3-mercaptopropyl]amino-3-[(3-methylphenyl)oxy]benzene N-[(2R)-2-amino-3-mercaptopropyl]amino-4-[(3-(hydroxymethyl)phenyl)oxy]benzene N-[(2R)-2-amino-3-mercaptopropyl]amino-2-methyl-4-(phenoxy)benzene 2-[2(R)-amino-3-mercaptopropylamino]-N-(3-methylphenyl)-benzamide or the disulfide or pharmaceutically acceptable salts thereof.

Examples of the compounds of this invention are as follows:

3-[2(S)-Amino-3-mercaptopropylamino]-N-(2,3-dimethylphenyl)benzamide

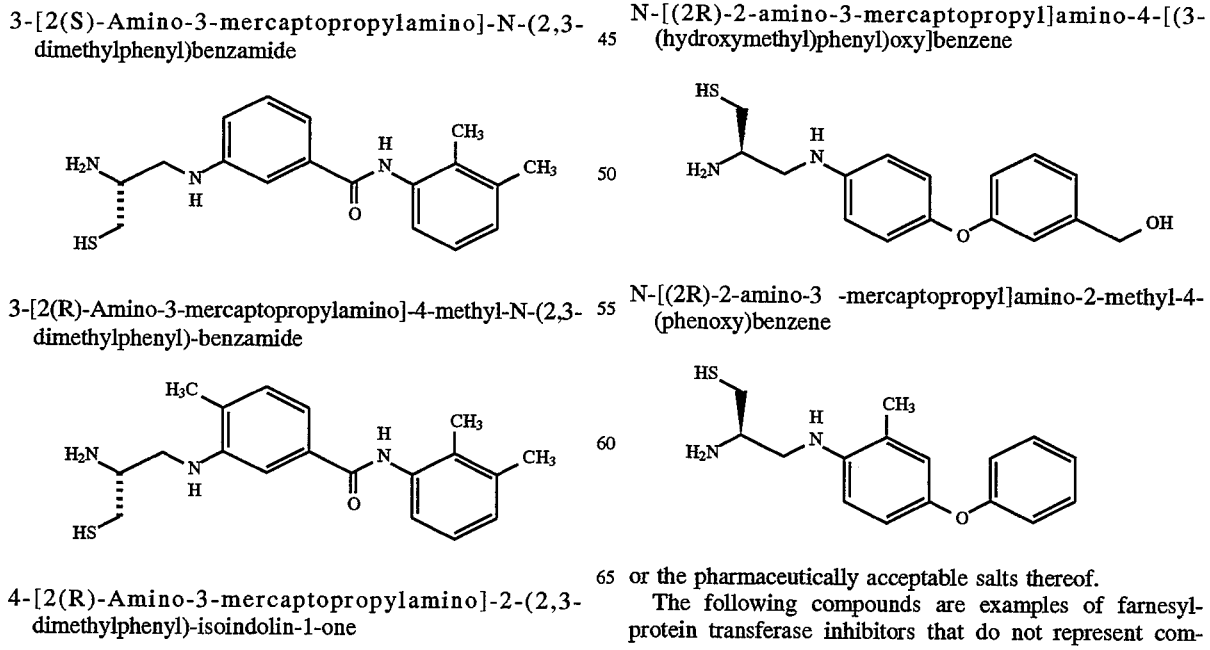

3-[2(R)-Amino-3-mercaptopropylamino]-4-methyl-N-(2,3-dimethylphenyl)-benzamide

4-[2(R)-Amino-3-mercaptopropylamino]-2-(2,3-dimethylphenyl)-isoindolin-1-one

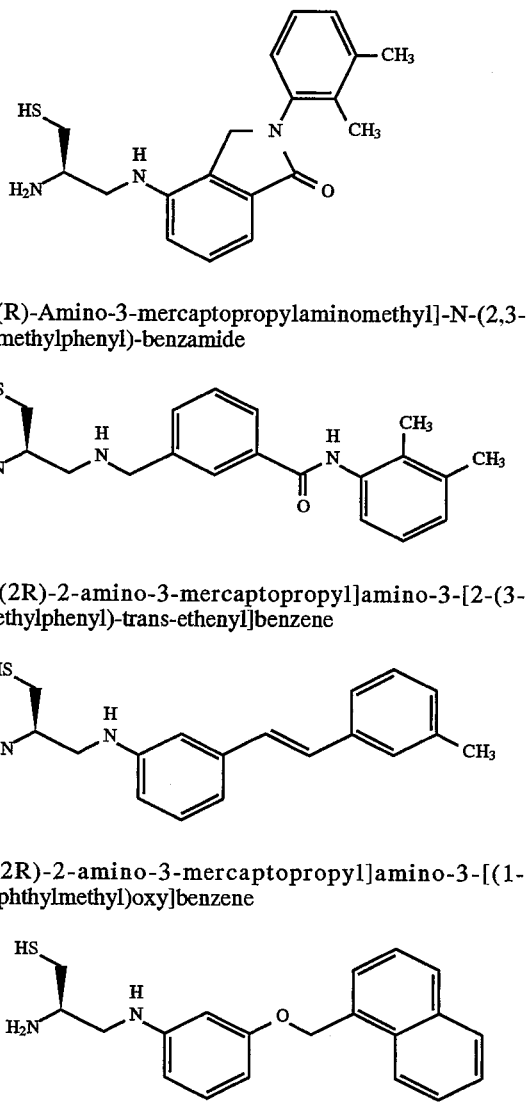

3-[2(R)-Amino-3-mercaptopropylaminomethyl]-N-(2,3-dimethylphenyl)-benzamide

[N-[(2R)-2-amino-3-mercaptopropyl]amino-3-[2-(3-methylphenyl)-trans-ethenyl]benzene N-[(2R)-2-amino-3-mercaptopropyl]amino-3-[(1-naphthylmethyl)oxy]benzene N-[(2R)-2-amino-3-mercaptopropyl]amino-4-[(3-(hydroxymethyl)phenyl)oxy]benzene N-[(2R)-2-amino-3 -mercaptopropyl]amino-2-methyl-4-(phenoxy)benzene or the pharmaceutically acceptable salts thereof.

The following compounds are examples of farnesyl-protein transferase inhibitors that do not represent compounds of the instant invention because they incorporate a carboxylic acid moiety at the C-terminus of the molecule. Such compounds might require development of a prodrug strategy to provide in vivo efficacy:

N-[(2R)-2-amino-3-mercaptopropyl]amino-3-[(3-carboxyphenyl)oxy]benzene
N-[(2R)-2-amino-3-mercapto-1-oxopropyl]amino-3-[(3-carboxyphenyl)oxy]benzene
N-[(2R)-2-amino-3-mercapto-1-oxopropyl]amino-3-[(3-carbomethoxyphenyl)oxy]benzene
N-[(2R)-2-amino-3-mercapto-1-oxopropyl]amino-4-[(3-carbomethoxyphenyl)oxy]benzene
N-[(2R)-2-amino-3-mercapto-1-oxopropyl]amino-4-[(3-carboxyphenyl)oxy]benzene
N-[(2R)-2-amino-3-mercaptopropyl]amino-4-[(3-carboxyphenyl)oxy]benzene
N-[(2R)-2-amino-3-mercaptopropyl]amino-3-[(4-carboxyphenyl)oxy]benzene
N-[(2R)-2-amino-3-mercapto-1-oxopropyl]amino-4-[(4-carboxyphenyl)oxy]benzene
N-[(2R)-2-amino-3-mercaptopropyl]amino-4-[(4-carboxyphenyl)oxy]benzene.

The compounds of the present invention may have asymmetric centers and occur as racemates, racemic mixtures, and as individual diastereomers, with all possible isomers, including optical isomers, being included in the present invention. It is understood that the location of the "-V-Z" moiety in relation to the amino/aminoalkyl moiety in Formulas A and B may be ortho, meta or para and specific examples of the regioisomers are set forth in the Examples. The present invention further includes all disulfides of the claimed compounds, derived from two of the same compounds. When any variable (e.g. aryl, heterocycle, $R^1$, $R^2$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

As used herein, "aralkyl" is intended to mean any stable monocyclic, bicyclic or tricyclic carbon ring of up to 7 members in each ring, wherein at least one ring is aromatic, attached to the rest of the molecule via a straight or branched-chain saturated aliphatic hydrocarbon group having the specified number of carbon atoms. Examples of such aralkyl elements include benzyl, phenylethyl, naphthylmethyl, naphthylethyl, tetrahydronaphthylmethyl, indanylmethyl, biphenylmethyl and the like.

The term heterocycle or heterocyclic, as used herein, represents a stable 5- to 7-membered monocyclic or stable 8- to 11-membered bicyclic or stable 11-15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with I or 2 substitutents selected from the group which includes but is not limited to F, Cl, Br, $CF_3$, $NH_2$, $N(C_1-C_6$ alkyl$)_2$, $NO_2$, CN, $(C_1-C_6$ alkyl$)O-$, $-OH$, $(C_1-C_6$ alkyl$)S(O)_m-$, $(C_1-C_6$ alkyl$)C(O)NH-$, $H_2N-C(NH)-$, $(C_1-C_6$ alkyl$)C(O)-$, $N_3$, $(C_{16l}-C_6$ alkyl$)OC(O)NH-$ and $C_1-C_{20}$ alkyl.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^6$, $R^{11}$, etc.) at a particular location in a molecule be independent of its definitions elsewhere in that molecule. Thus, $-C(R^{11})_2$ represents $-CHH$, $-CHCH_3$, $-CHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Reaction Schemes 1-9, in addition to other standard manipulations such as ester hydrolysis, cleavage of protecting groups, etc., as may be known in the literature or exemplified in the experimental procedures. Substituents $R^a$ and $R^b$, as shown in the Schemes, represent the substituents $R^2$, $R^3$, $R^4$, and $R^5$; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Reaction Schemes.

Synopsis of Reaction Schemes 1–22:

The requisite intermediates useful in the preparation of the compounds of the instant invention are in some cases commercially available, or can be prepared according to well known literature procedures. In Scheme 1, for example, the synthesis of 3-aminobenzamides is outlined. 3-Nitrobenzoic acids I, available commercially or by procedures known to those skilled in the art, can be activated using a variety of agents such as EDC (1-ethyl-3-(3-dimethylaminopropyl)-carbodiimide) in a solvent such as methylene chloride, chloroform, dichloroethane, or in dimethylformamide and reacted with a suitably substituted amine. Subsequent catalytic hydrogenation provided the 3-aminobenzamide It. The product It is then reductively alkylated with protected cysteine aldehyde, which provides the compounds of formula A after appropriate deprotection.

Synthesis of compounds of the instant invention wherein a Z substituent which is a substituted amine and which is attached to the phenyl ring via a methylene linker is illustrated in Scheme 2. Thus, reaction of the appropriately substituted ortho-nitrobenzaldehyde yielded the amine Iit which is then appended with the cysteine residue.

Scheme 3 illustrates synthesis of the instant compounds wherein Z is an alkyl, aryl, alkenyl or heteroaryl group utilizing an appropriately substituted Grignard reagent with an activated benzoic acid which already incorporates a fully protected cysteine residue.

Schemes 4–15 illustrate the formation of various "V" spacer groups in the context of preparing aminodiphenyl intermediates in the synthesis of compounds of the formula A. Such intermediates can be reacted with bisprotected cysteine as shown in Schemes 1 and 2 to provide the instant compounds. The Schemes illustrate the formation of such intermediates wherein the "Z" substituent is phenyl, but it is understood that as such Schemes 4–15 are illustrative only and such reactions as shown are equally useful in preparing compounds of formula A wherein the "Z" substituent is other than phenyl.

Schemes 4–7 illustrate use of Ullman reactions to provide diphenyl ethers, amines and sulfides from readily available fully substituted phenols/thiol/anilines and aryl halides. In such syntheses, the desired amine moiety is typically masked as a nitro group which is subsequently reduced by techniques well known in the art. An alternative synthesis of the diphenyl ethers which employs para-nitro fluorobenzene is shown in Scheme 8.

Scheme 9 illustrates coupling of suitably substituted anilines with readily available phenylsulfonyl chlorides. Access to aminobenzophenones is illustrated in Scheme 10, which also illustrates the reduction of the carbonyl to provide the unsubstituted methyl spacer. Also shown in Scheme 10 is reductive amination of the resulting carbonyl to provide the amine substituted methyl spacer. Another methods of forming the benzophenone intermediates, illustrated in Scheme 11, is a Stille reaction with an aryl stannane.

Schemes 12 and 13 illustrate palladium mediated formation of olefin and acetylene spacer units. Scheme 14 illustrates formation of an appropriately substituted benzyl ether. Scheme 15 illustrates the use of the Claisen rearrangement to provide methyl spacers having substituents such as a vinyl group which can itself be further functionalized.

Preparation of the cyclic compounds of the formula D is illustrated in Scheme 16. The 2-methyl-3-nitrobenzoic acid IV is esterified, then photolytically halogenated to provide the ester IV. Reaction of compound V with an appropriately substituted primary amine results in the 6-nitro-isoindolinone VI, which is processed as described for Scheme 1 and 2 to provide the compounds of the instant invention. Use of a suitably substituted 2-methyl-5-nitrobenzoic acid VII provides the analogous instant compound of formula C, as illustrated in Scheme 17.

The synthesis of an example of a compound of formula B is illustrated in Scheme 18. A suitably substituted indoline VIII is halogenated to provide a separable mixture of 6-bromo and 4-bromoindolines. The 6-bromoindoline is protected and carbomethoxylated to provide the ester IX which undergoes the sequence of reactions previously described to provide compound X.

Scheme 19 illustrates the synthesis of compounds having the formula B but with a different substitution pattern than illustrated in Scheme 16.

Synthetic methods of incorporating ring substituents on the phenyl ring of the instant compounds starting with the readily accessible phenyl halides XI are illustrated in Schemes 20 and 21. In both Schemes, $R^c$-alkyl represents a substituent such as $R^3$ or $R^4$.

Scheme 22 illustrates the synthesis of the homologous aminomethylphenyl compound of formula A.

SCHEME 1

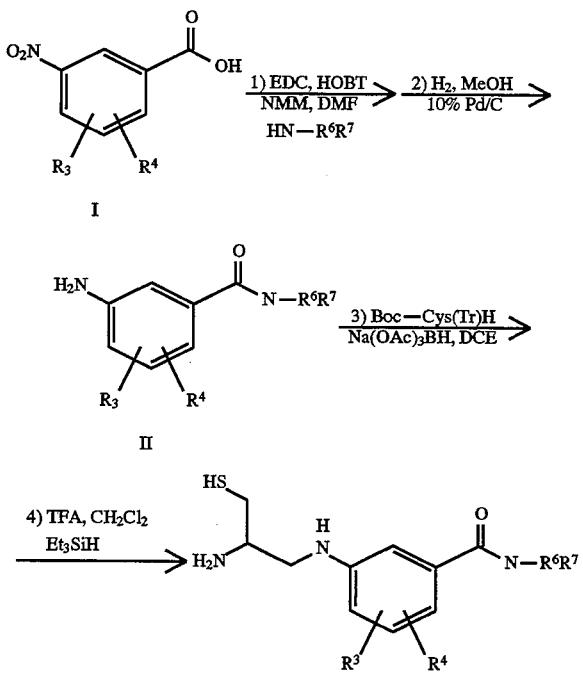

SCHEME 2

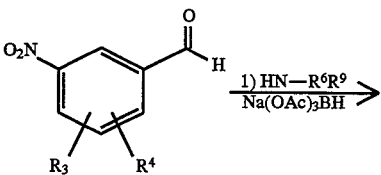

-continued
SCHEME 2
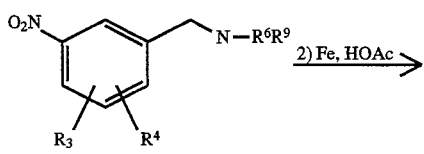
III
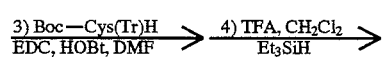
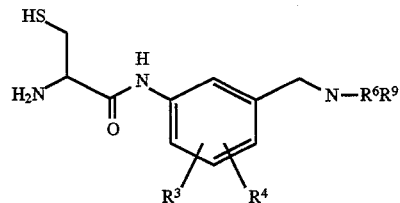
SCHEME 3
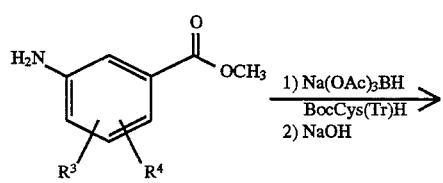
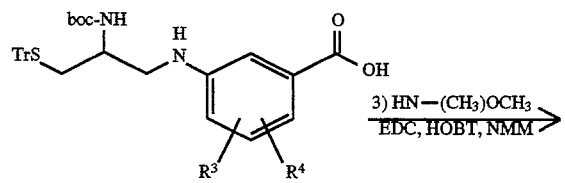
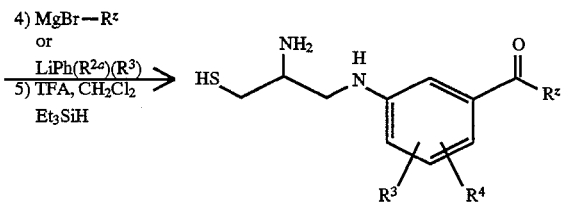
wherein $R^z$ is Z which is $C_1$–$C_8$ alkyl, $C_2$–$C_8$ alkenyl, aryl or heterocycle
SCHEME 4
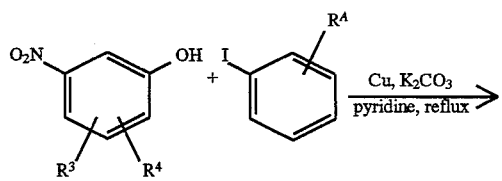
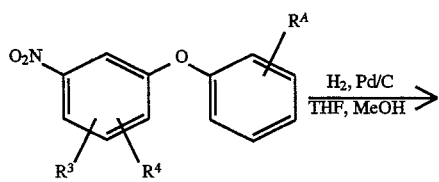
-continued
SCHEME 4
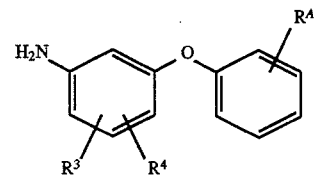
SCHEME 5
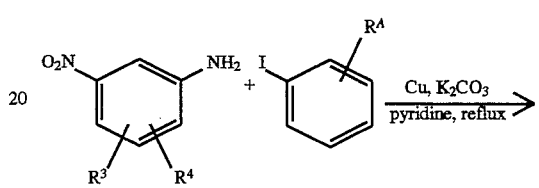
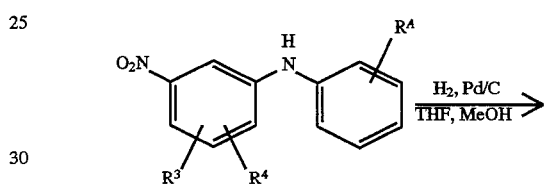
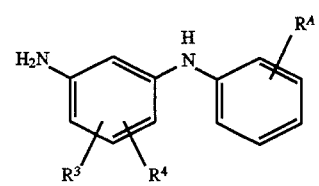
SCHEME 6
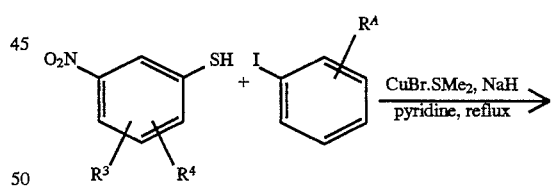
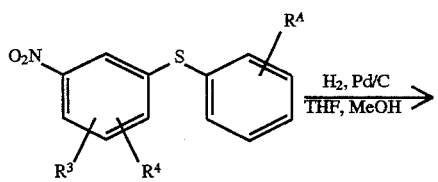
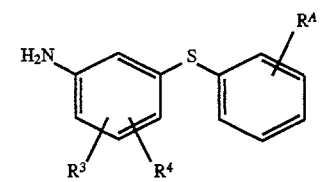

SCHEME 7
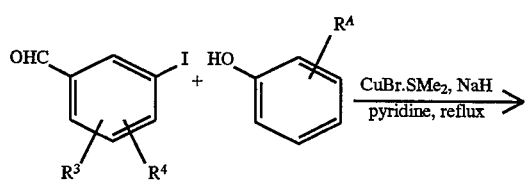
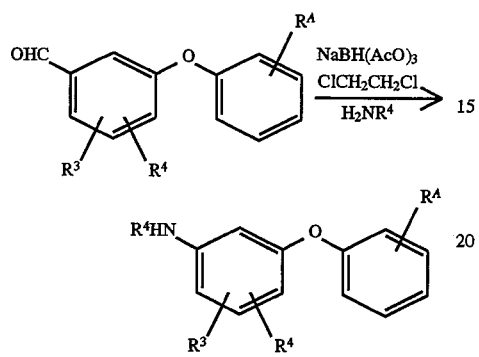
SCHEME 8
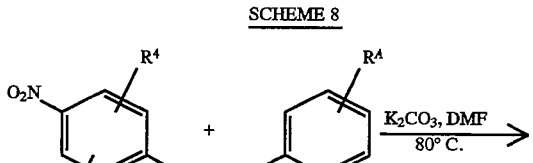
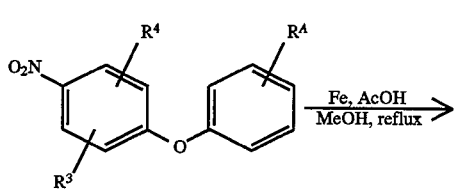
SCHEME 8 -continued
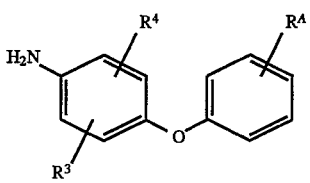
SCHEME 9
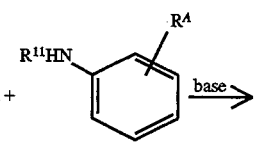
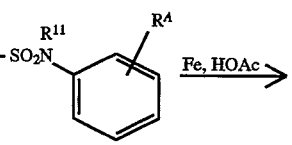
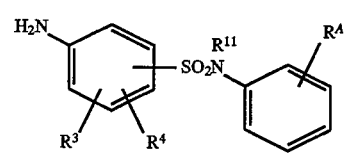
SCHEME 10
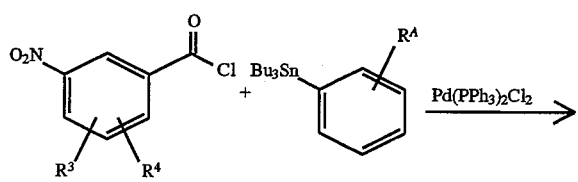
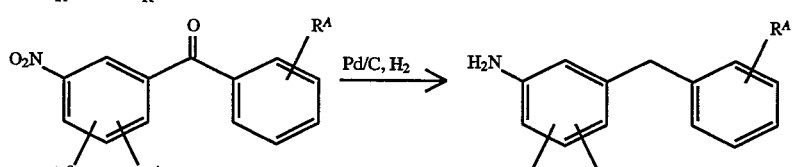
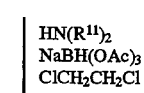

-continued
SCHEME 10
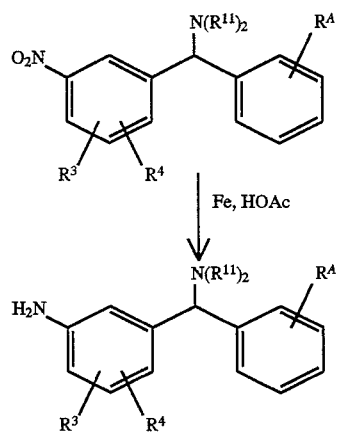
SCHEME 11
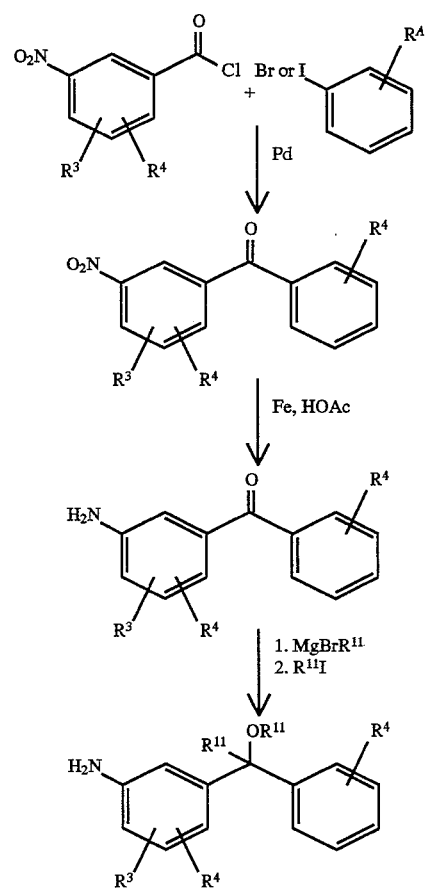
SCHEME 12
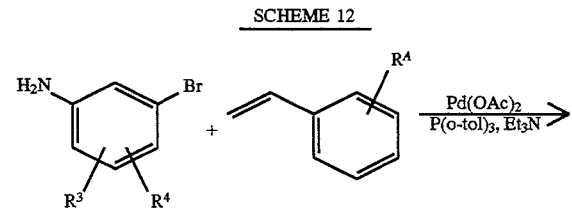
-continued
SCHEME 12
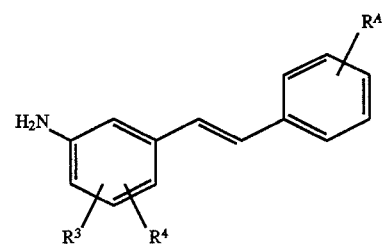
SCHEME 13
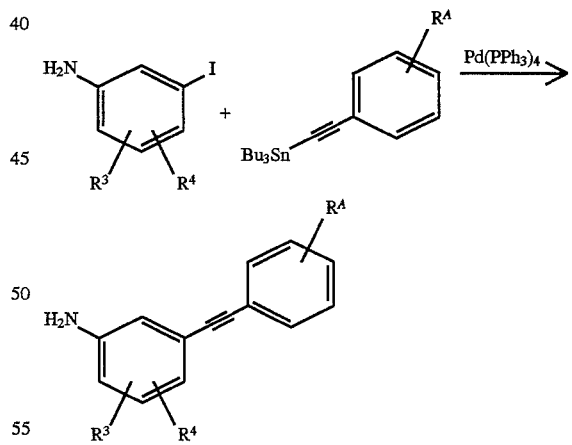
SCHEME 14
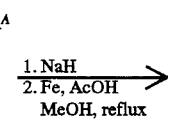

-continued
SCHEME 14
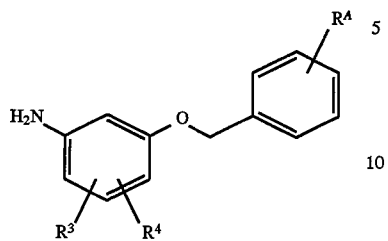
SCHEME 15
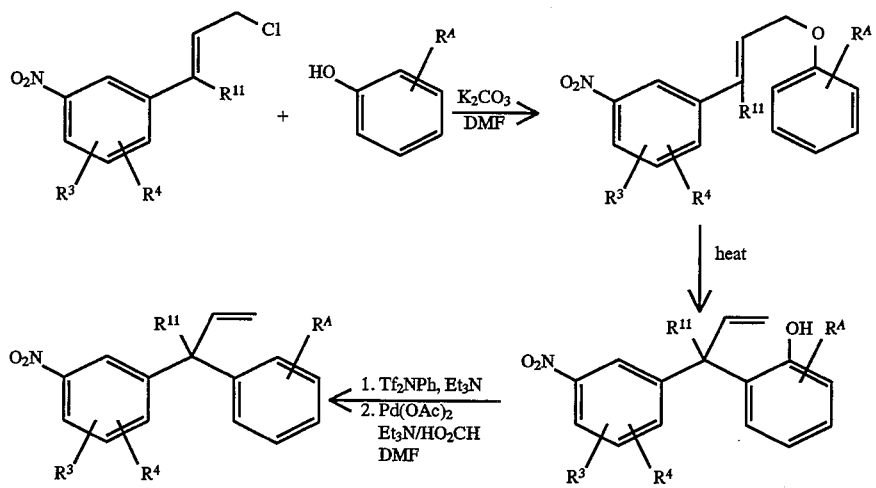
SCHEME 16
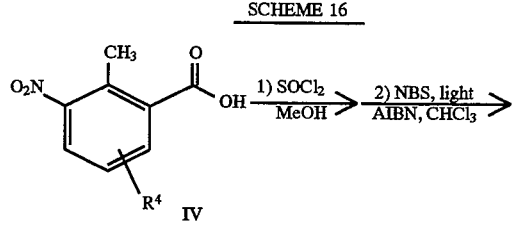
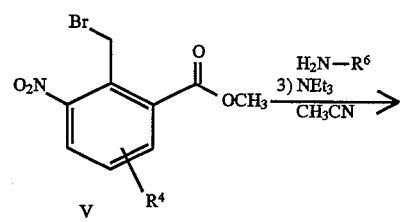
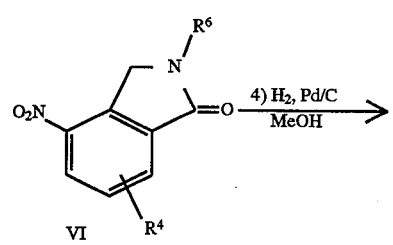
5) Boc-Cys(Tr)H
Na(OAc)₃BH, DCE → 6) TFA, CH₂Cl₂
Et₃SiH →
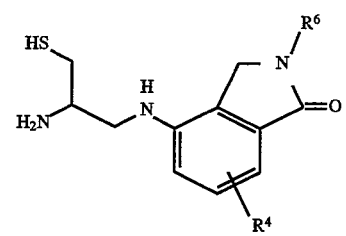
-continued
SCHEME 16
SCHEME 17
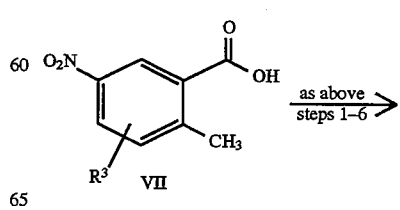
as above
steps 1–6 →

25
-continued
SCHEME 17
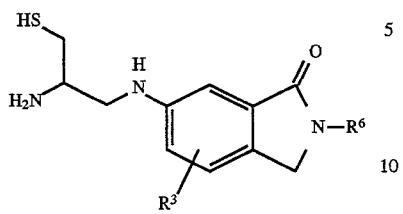
SCHEME 18
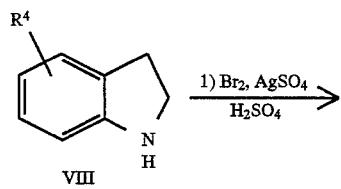
6-Br-indoline:4-Br-indoline
10:1
prep HPLC separated
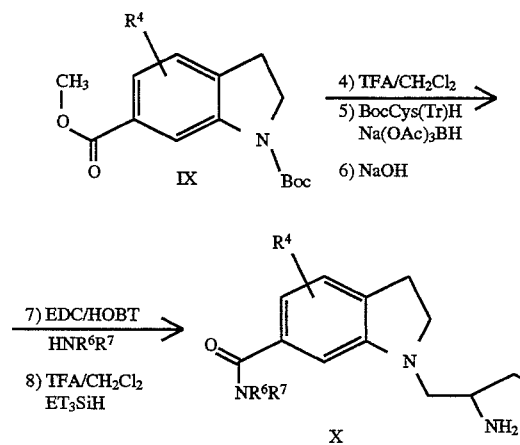
SCHEME 19
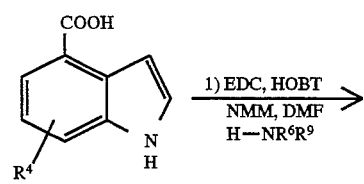
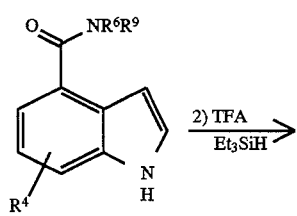
26
-continued
SCHEME 19
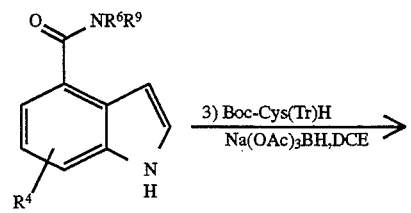
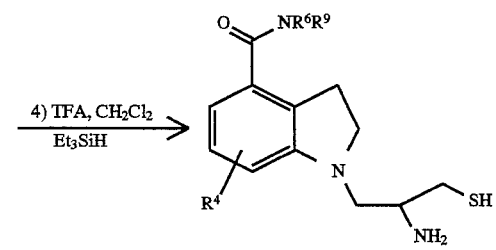
SCHEME 20
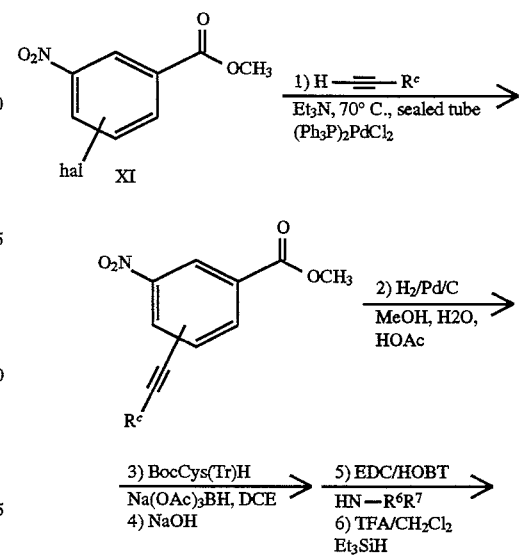
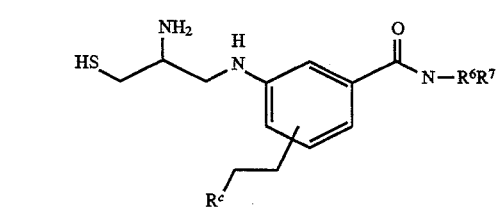
SCHEME 21
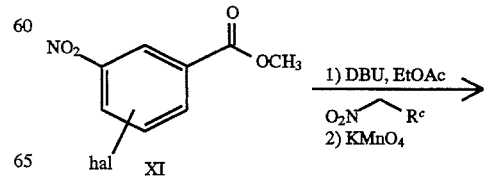

27

-continued
SCHEME 21

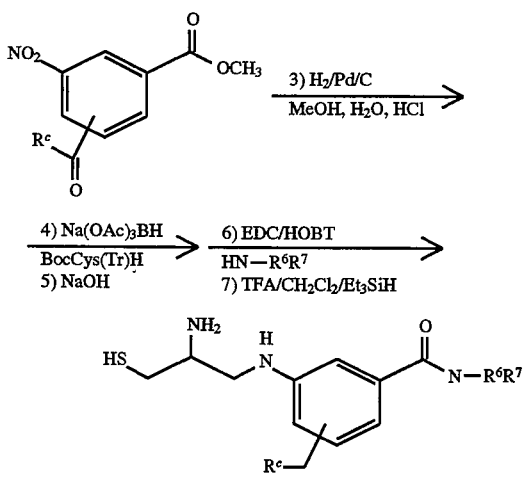

SCHEME 22

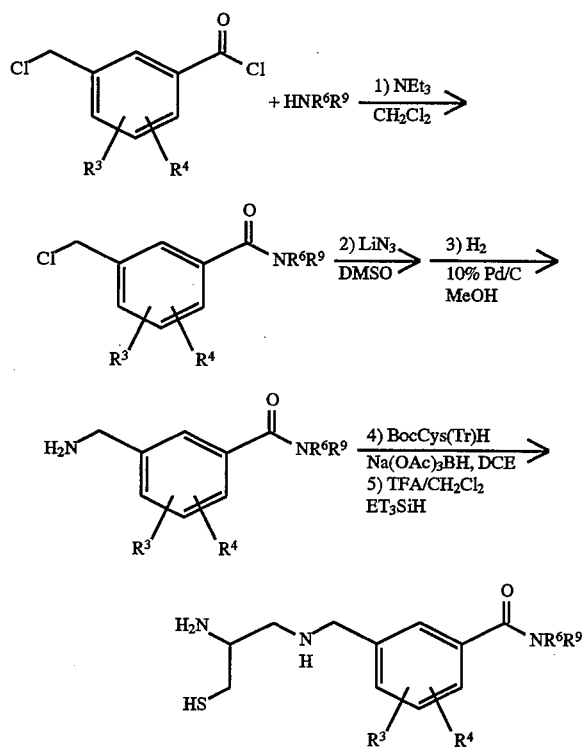

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Synthetic experimental descriptions are also provided for compounds which are not part of the instant invention for the purposes of illustrating reactions that would be generally useful for preparing the instant compounds. Particular materials employed, species and conditions are intended to be further illustrative of the invention and not limitative of the reasonable scope thereof. Purification by HPLC was accomplished with a 40×100 mm Waters PrepPak® reverse phase HPLC column (Delta-Pak™ $C_{18}$ 15 µm, 100 Å). Gradient elution employed 0.1% trifluoroacetic acid in water (Solvent A) and 0.1% trifluoroacetic acid in acetonitrile (Solvent B). Chloride salts were obtained by passing an aqueous solution of the trifluoroacetic acid salt through a Biorad AG® 3×4 ion exchange resin column (100–200 mesh, Cl-form). Purification by HPLC was utilized for each of the Examples 1–22 as set forth below.

EXAMPLE 1

3-[2(R)-Amino-3-mercaptopropylamino]-N-(2,3-dimethylphenyl)benzamide (4)

Step 1: Preparation of 3-nitro-N-(2,3-dimethylphenyl)benzamide (1)

To a solution of 3-nitrobenzoic acid (3.0 g ) and 2,3-dimethylaniline (2.17 g) in 20 mL of DMF was added 1-hydroxybenzotriazole (2.75 g), EDC (3.44 g) and triethylamine (7.39 mL). The resulting solution was stirred for 16 h. The DMF was evaporated in vacuo and the residue was partitioned with ethyl acetate and water. The ethyl acetate layer was extracted w/50 mL each of 2% potassium hydrogen sulfate, saturated sodium bicarbonate, saturated sodium chloride, dried over magnesium sulfate and concentrated in vacuo to afford the title compound as a solid. NMR (300 MHz, $CDCl_3$) δ 8.72 (1H, s), 8.40 (1 H, d, J=6 Hz), 8.26 (1H, d, J=9 Hz), 7.93 (IH, s), 7.69 (1H, t, J=9 Hz), 7.45 (1 H,d, J=9 Hz), 7.14 (1H, t, J=8 Hz), 7.08 (1H, d, J=9 Hz), 2.32 (3H, s), 2.21 (3H, s).

Step 2: Preparation of 3-amino-N-(2,3-dimethylphenyl)benzamide (2)

To a solution of 1 (1 g) in 70 mL methanol and 30 mL of tetrahydrofuran was added 10% Pd/C (0.2 g) under nitrogen atmosphere. Hydrogen was applied to the mixture at 60 psi for 16 h. The mixture was filtered and concentrated in vacuo to obtain the product. NMR (300 MHz, $CDCl_3$) δ 7.71 (1H, s), 7.55 (1H, d, J=9 Hz), 7.23 (1H, t, J=9 Hz), 7.19 (1H, s), 7.14 (1H, t, J=9 Hz), 7.04 (1H, d, J=9 Hz), 6.82 (1H, d, J=9 Hz), 3.84 (2H, b), 2.32 (3H, s), 2.20 (2H, s).

Step 3: Preparation of 3-[2(R)-(t-butyloxycarbonylamino)-3-(triphenylmethyl-mercapto)propylamino ]-N-(2, 3-dimethylphenyl) benzamide (3)

To a solution of 2 (0.28 g) in 12 mL of 1,2-dichloroethane at 0° C. was added sodium triacetoxyborohydride (0.36 g) and N-t-butyloxycarbonyl-S-(triphenyl- methyl)cysteinal (0.35 g). The cooling bath was removed and the mixture was stirred for 4 h at 20° C. The solution was concentrated in vacuo and the residue was partitioned between ethyl acetate and water. The ethyl acetate layer was extracted with 50 mL each of 2% potassium hydrogen sulfate, saturated sodium bicarbonate, saturated sodium chloride, dried over magnesium sulfate and concentrated in vacuo to afford the title compound as a foam. NMR (300 MHz, $CDCl_3$) δ 8.17 (1H, b), 7.46–7.18 (15H, m), 6.60 (1H, m), 3.13(2H, m,), 2.45 (3H, m), 2.30 (3H, s), 2.18 (3H, s), 1.42 (9H, s).

Step 4: 3-[2(R)-Amino-3-mercaptopropyl-amino]N-(2,3-dimethylphenyl)benzamide dihydrochloride (4)

To a solution of 3 (0.410 g ) in 10 mL of methylene chloride was added triethylsilane (0.200 g ) and 5 mL of trifluoroacetic acid. The solution was stirred for 45 min, evaporated in vacuo, and partitioned with hexane and 0.1% trifluoroacetic acid in water:methanol 2:1. The 0.1% trifluoroacetic acid/water: methanol solution was injected directly onto a Delta-Pak (C-18, 100 Å, 15 mm, 40mm×100mm) prep HPLC column. The gradient at 40 mL/min. was 100%A (0.1% trifluoroacetic acid/water) for 5 min. followed by 85% A to 50%A in 60 min. with B as 0.1% trifluoroacetic acid/acetonitrile. The pure fractions were pooled, evaporated in vacuo to near dryness, and then taken up in 5 mL of water. This water solution was passed through a 1.2 g column of Bio-Rad AG 3-X4 chloride anion exchange resin with water rinses. The resulting aqueous column eluant was lyophillized 20 h to yield the title compound as a solid. NMR (300 MHz, $CD_3OD$)δ 7.30 (3H, m), 7.12 (3H, s), 6.97 (1H, m), 3.30 (3H, m), 2.90 (2H, m ), 2.30 (3H,s), 2.18 (3H, s).

Using the appropriate starting materials the methods described above for Example 1 were used to prepare the following examples.

EXAMPLE 2

3-[2(R)-Amino-3-mercaptopropylamino]-N-phenyl-N-methylbenzamide dihydrochloride

Analysis Calculated for $C_{17}H_{21}N_3OS$•3.4 HCl•0.4 $H_2O$: C, 45.79; H, 5.70; N, 9.42; Found: C, 45.85; H, 5.68; N, 9.78.

EXAMPLE 3

3-[2(R)-Amino-3-mercaptopropylamino]-N-(1-naphthylmethyl)-benzamide dihydrochloride Analysis Calculated for $C_{21}H_{23}N_3OS$•2.2 HCl•0.7 $H_2O$: C, 55.05; H, 5.85; N, 9.17; Found: C, 54.99; H, 5.86; N, 9.32.

EXAMPLE 4

3-[2(R)-Amino-3-mercaptopropylamino]-N-phenylbenzamide dihydrochloride

Analysis Calculated for $C_{16}H_{19}N_3OS$•2.0 HCl•0.2 $H_2O$ C, 50.85; H, 5.71; N, 11.12; Found: C, 50.86; H, 5.80; N, 11.16.

EXAMPLE 5

3-[2(R)-Amino-3-mercaptopropylamino]-N-benzylbenzamide dihydrochloride

Analysis Calculated for $C_{17}H_{21}N_3OS \cdot 2.0\ HCl \cdot 1.1\ H_2O$ C, 50.03; H, 6.22; N, 10.29; Found: C, 50.08; H, 6.02; N, 10.44.

EXAMPLE 6

3-[2(S)-Amino-3-mercaptopropylamino]-N-(2,3-dimethylphenyl)-benzamide dihydrochloride Analysis Calculated for $C_{18}H_{23}N_3OS \cdot 2.2HCl \cdot 0.1H_2O$ C, 52.55; H, 6.22; N, 10.21; Found: C, 52.55; H, 6.13; N, 10.26.

EXAMPLE 7

3-[2(R)-Amino-3-mercaptopropanoylamino]-N-(2,3-dimethylphenyl)benzamide hydrochloride Analysis Calculated for $C_{18}H_{21}N_3O_2S \cdot 1.3HCl \cdot 0.3H_2O$ C, 53.85; H, 5.67; N, 10.47; Found: C, 53.79; H, 5.70; N, 10.23.

EXAMPLE 8

3-[2(R)-Amino-3-mercaptopropylamino]-4-methyl-N-(2,3-dimethylphenyl)-benzamide dihydrochloride Analysis Calculated for $C_{19}H_{25}N_3OS \cdot 2.0HCl$ C, 54.80; H, 6.54; N, 10.09; Found: C, 54.86; H, 6.65; N, 9.88.

EXAMPLE 9

3-[2(R)-Amino-3-mercaptopropylamino]-4-methoxy-N-(2,3-dimethylphenyl)-benzamide dihydrochloride Analysis Calculated for $C_{19}H_{25}N_3O_2S \cdot 2.2HCl \cdot 0.3H_2O$: C, 51.07; H, 6.25; N, 9.40; Found: C, 50.97; H, 6.24; N, 9.49.

EXAMPLE 10

3-[2(R)-Amino-3-mercaptopropylamino]-6-methyl-N-(2,3-dimethylphenyl)-benzamide hydrochloride Analysis Calculated for $C_{19}H_{25}N_3OS \cdot 1.3\ HCl \cdot 0.1\ H_2O$ C, 58.13; H, 6.80; N, 10.70; Found: C, 58.06; H, 6.69; N, 10.57.

EXAMPLE 11

3-[2(R)-Amino-3-mercaptopropylamino]-N-[1-(5,6,7,8-tetrahydronaphthyl)]-benzamide dihydrochloride Analysis Calculated for $C_{20}H_{25}N_3OS \cdot 2.0\ HCl \cdot 0.8\ H_2O$ C, 54.25; H, 6.51; N, 9.49; Found: C, 54.23; H, 6.22; N, 9.61.

EXAMPLE 12

1-[3-[2(R)-Amino-3-mercaptopropylamino] phenylcarbonyl]indoline dihydrochloride

Analysis Calculated for $C_{18}H_{21}N_3OS \cdot 2.3\ HCl \cdot 0.9\ H_2$) C, 50.59; H, 5.92; N, 9.83; Found: C, 50.56; H, 5.90; N, 9.53.

EXAMPLE 13

1-[2(R)-Amino-3-mercaptopropylamino]-3-[(2,3-dimethylbenzoyl)amino]-benzene dihydrochloride Analysis Calculated for $C_{18}H_{23}N_3OS \cdot 2.5\ HCl \cdot 0.8\ H_2O$ C, 49.72; H, 6.28; N, 9.66; Found: C, 49.70; H, 6.25; N, 9.68.

EXAMPLE 14

4-[2(R)-Amino-3-mercaptopropylamino]-2-(2,3-dimethylphenyl)isoindolin-1-one dihydrochloride (10)

Step 1: Preparation of Methyl 2-methyl-3-nitrobenzoate (5)

A solution of 2-methyl-3-nitrobenzoic acid (5 g) and thionyl chloride (40 mL) was refluxed for 3 h in methanol (150 mL). The solution was concentrated in vacuo and the residue was partitioned between ethyl acetate and saturated sodium bicarbonate. The ethyl acetate layer was washed with saturated sodium chloride, dried over magnesium sulfate, and concentrated in vacuo to afford the the product as a solid. NMR (300 MHz, $CDCl_3$) δ 7.99 (1H, d), 7.85 (1H, d), 7.38 (1H, t), 3.92 (3H, s), 2.62 (3H, s).

Step 2: Preparation of Methyl 2-bromomethyl-3-nitrobenzoate (6)

To a solution of 5 (1 g) in chloroform (70 mL) was added N-bromosuccinimide (0.82 g) and azobis(isobutyronitrile) (0.010 g). A light source was directed onto the flask and the mixture was refluxed for 18 h. The solution was cooled to 0° C., a precipitate was filtered, and flitrate was concentrated in vacuo to obtain the crude product. Purification on silica gel with hexane/ethyl acetate 9/1 afforded the product as a solid. NMR (300 MHz, $CDC_3$) δ 8.10 (1H, d, J=9 Hz), 7.95 (1H,d, J=9 Hz), 7.54 (1H,t, J=9 Hz), 5.14 (2H, s), 3.99 (3H, s).

Step 3: Preparation of 2-(2,3-Dimethylphenyl)-4-nitroisoindolin-1-one (7)

A solution of 6 ( 0.140 g), 2,3 - dimethylphenyl aniline (0.065 mL), and triethyl-amine (0.142 mL) in acetonitrile (10 mL) was refluxed 18 h. The solution was concentrated in vacuo and the residue was partitioned between methylene chloride and 2% potassium hydrogen sulfate. The methylene chloride was washed with saturated sodium chloride, dried over magnesium sulfate, and concentrated in vacuo to afford the the product as a solid. NMR (300 MHz, $CDCl_3$) δ 8.46 (1H, d, J=8 Hz), 8.30 (1H, d, J=8 Hz), 7.77 (1H, t, J=8 Hz), 7.24 (1H, s ), 7.22 (1H, d, J=2 Hz), 7.12 (1H, m), 5.18 (2H, s), 2.35 (3H, s), 2.14(3H, s).

Step 4: Preparation of 4-Amino-2-(2,3-dimethylphenyl)-isoindolin-1-one (8)

To a solution of 7 (0.110 g ) in 15 mL methanol was added 10% Pd/C (0.020 g) under nitrogen atmosphere. Hydrogen was applied to the mixture at 1 atmosphere for 2 h. The mixture was filtered and concentrated in vacuo to obtain the product. NMR (300 MHz, $CDCl_3$) δ 7.41 (1H, d, J=6 Hz), 7.33 (1H, t, J=6 Hz), 7.18 (1H, s), 7.16 (1H, d, J=2 Hz), 7.10 (1H, t, J=4 Hz), 6.69 (1H, d, J=6 Hz), 4.54 (2H, s), 3.75 (2H, b), 2.33 (3H, s), 2.12 (3H, s).

Step 5: Preparation of 2-(2,3-Dimethylphenyl)-4-[2(R)-(t-butyloxycarbonyl-amino)-3-triphenylmethyl-mercaptopropylamino]isoindolin-1-one (9)

Compound 9 was prepared from 8 (0.103 g) using methods described in Step 3. of Example 1 and used in the next step without purification.

Step 6: Preparation of 4-[2(R)-Amino-3-mercaptopropyl-amino]-2-(2,3-dimethylphenyl) isoindolin-1-one dihydrochloride (10)

The above compound was prepared from 9 using methods described in Step 4 of Example 1.

NMR (300 MHz, $CD_3OD$) δ 7.45 (1H, m), 7.3–7.1 (4H, m), 7.0 (1H, m), 4.70 (2H, s), 3.63 (2H, m), 3.53 (1H, m), 2.36 (3H, s), 2.11 (3H, s).

Using the appropriate starting materials the methods described above for Example 14 were used to prepare the following example.

EXAMPLE 15

4-[2(R)-Amino-3-mercaptopropylamino]-2-benzylisoindolin-1-one hydrochloride

Analysis Calculated for $C_{18}H_{21}N_3OS \cdot 1.5$ $HCl \cdot 0.3$ $H_2O$: C, 55.82; H, 6.01; N, 10.85; Found: C, 55.88; H, 6.01; N, 10.81.

EXAMPLE 16

1-[2(R)-Amino-3-mercaptopropylamino]-N-(2,3-dimethylphenyl)-4-indoline carboxamide dihydrochloride (14)

Step 1: Preparation of N-(2,3-Dimethylphenyl)-4-indole carboxamide (11)

Starting with indole-4-acetic acid (0.20 g) the above compound was prepared using the method described in Step 1, of Example 1. NMR (300 MHz, $CDCl_3$) δ 8.51 (1H, s), 7.83 (1H, s), 7.72 (1H, d, J=8 Hz), 7.65 (1H, d, J=8 Hz), 7.58 (1H, d, J=8 Hz), 7.37 (1H, t, J=3 Hz), 7.30 (1H, d, J=8 Hz), 7.18 (1H, t, J=8 Hz), 7.06 (2H, m), 2.35 (3H, s), 2.25 (3H, s).

Step 2: Preparation of N-(2,3-Dimethylphenyl)-4-indoline carboxamide (12)

To compound 11 (0.15 g) was added triethylsilane (0.36 mL) and trifluoroacetic acid (10 mL). After stirring for 10 min. the solution was concentrated in vacuo and the residue was partitioned between ethyl acetate and sodium bicarbonate. The ethyl acetate layer was washed with saturated sodium chloride, dried over magnesium sulfate and concentrated in vacuo to afford the crude product. Trituration with hexane/ethyl acetate 8/2 gave the product. NMR (300 MHz, $CDCl_3$) δ 7.62 (1H, d, J=3 Hz), 7.53 (1H, s), 7.13 (2H, q, J=3 Hz), 7.04 (2H, m), 6.77 (1H, d, J=3 Hz), 3.62 (2H, t, J=3 Hz), 3.39 (2H, t, J=3 Hz), 2.33 (3H, s), 2.21 (3H, s).

Step 3: Preparation of 1-[2(R)-(t-butyloxycarbonyl-amino)-3-(triphenylmethylmercapto)propylamino]-N-(2,3-dimethylphenyl)-4-indoline carboxamide (13)

The above compound was prepared from 12 (0.12 g) using the method described in Step 3. of Example 1 and used in the next step without purification. NMR (300 MHz, $CDCl_3$) δ 7.63 (1H, d, J=4 Hz), 7.52 (1H, s), 7.46–7.20 (15H, m), 7.04 (1H, d, J=4 Hz), 6.92 (1H, d, J=4 Hz), 6.55 (1H, d, J=4 Hz), 4.58 (1H, m), 3.80 (1H, m), 3.30 (3H, m), 3.05 (2H, m), 2.40 (2H, m), 2.33 (3H, s), 2.20 (3H, s), 1.42 (9H, s).

Step 4: Preparation of 1-[2(R)-amino-3-mercaptopropylamino]-N-(2,3-dimethylphenyl)-4-indoline carboxamide dihydrochloride (14)

The above compound was prepared from 13 (0.35 g) using the method described in Step 4. of Example 1. FAB mass spectrum m/e 356 (m+1).

Analysis Calculated for $C_{20}H_{25}N_3OS \cdot 2.0$ $HCl \cdot 0.4$ $H_2O$: C, 55.14; H, 6.43; N, 9.65; Found: C, 55.08; H, 6.67; N, 9.83.

EXAMPLE 17

1-[2(R)-Amino-3-mercaptopropyl-amino]-3-[(2,3-dimethylphenyl)aminomethyl]-benzene hydrochloride (18)

Step 1: Preparation of 3-[(2,3-Dimethylphenyl)amino-methyl]nitrobenzene (15)

Starting with 3-nitrobenzaldehyde (0.50 g) and 2,3-dimethylphenylaniline (0.40 mL) the method described in Step 3. of Example 1 was used to prepare the above compound. NMR (300 MHz, $CDCl_3$) δ 8.25 (1H, s), 8.12 (1H, d, J=7 Hz), 7.72 (1H, d, J=7 Hz), 7.50 (1H, t, J=8 Hz), 6.95 (1H, t, J=8 Hz), 6.62 (1H, d, J=7 Hz), 6.36 (1H, d, J=7 Hz), 4.50 (2H, s), 4.09 (1H, s), 2.30 (3H, s), 2.13 (3H, s).

Step 2: Preparation of 3-[(2,3-Dimethylphenyl)amino-methyl]aniline (16)

To a solution of 15 (0.40 g) in ethanol (8 mL) was added elemental iron (Fe) (0.31 g) and acetic acid (0.66 g). The mixture was refluxed for 18 h. The mixture was filtered, concentrated in vacuo and the residue was partitioned between ethyl acetate and water. The ethyl acetate layer was extracted with saturated sodium bicarbonate, saturated sodium chloride, dried over magnesium sulfate and concentrated in vacuo to afford the title compound as an oil. NMR (300 MHz, $CDCl_3$) δ 7.13 (1H, t, J=3 Hz), 6.99 (1H, t, J=3 Hz), 6.77 (1H, d, J=3 Hz), 6.72 (1H, s), 6.60 (2H, d, J=3 Hz), 6.50 (1H, d, J=3 Hz), 4.25 (2H, s), 3.85 (1H, s), 3.65 (1H, s), 2.29 (3H, s), 2.05 (3H, s).

Step 3: Preparation of 1-[2(R)-(t-butyloxycarbonylamino)-3-(triphenyl-methylmercapto)propylamino]-3-[(2,3-dimethylphenyl)aminomethyl]benzene (17)

Starting with 16 (0.12 g) the method described in Step 3. of Example 1 was used to prepare the above compound. NMR (300 MHz, $CDCl_3$) δ 7.46–7.16 (15H, m), 7.11 (1H, t, J=8 Hz), 6.99 (1H, t, J=8 Hz), 6.69 (1H, d, J=8 Hz), 6.59 (1H, d, J=8 Hz), 6.53 (2H, d, J=3 Hz), 6.45 (1 H, m), 4.55 (1H, m), 4.24 (2H, s), 3.81 (2H, s), 3.70 (1H, s), 3.05 (2H, t), 2.44 (2H, d), 2.28 (3H, s), 2.05 (3H, s), 1.41 (9H, s).

Step 4: Preparation of 1-[2(R)-Amino-3-mercaptopropylamino]-3-[(2,3-dimethylphenyl)aminomethyl]benzene hydrochloride (18)

Starting with 17 (0.23 g) the method described in Step 4. of Example 1 was used to prepare the title compound. FAB mass spectrum m/e 314 (m+1).

Analysis Calculated for $C_{18}H_{25}N_3S \cdot 1.0\ HCl \cdot 0.4\ H_2O$: C, 60.20; H, 7.52; N, 11.70; Found: C, 60.27; H, 7.34; N, 11.54.

EXAMPLE 18

3-[2(R)-Amino-3-mercaptopropylaminomethyl]-N-(2,3-dimethylphenyl) benzamide dihydrochloride (23).

Step 1: Preparation of 3-chloromethyl-N-(2,3-dimethylphenyl)-benzamide (19)

To a solution of 3-chloromethylbenzoyl chloride (2.0 g) in methylene chloride (20 mL) was added 2,3- dimethylphenylaniline (1.28 g) and triethylamine (1.47 mL). The solution was stirred 18 h, concentrated in vacuo, and the residue was partitioned between ethyl acetate and water. The ethyl acetate layer was extracted w/50 mL each of 2% potassium hydrogen sulfate, saturated sodium bicarbonate, saturated sodium chloride, dried over magnesium sulfate and concentrated in vacuo. Upon concentration a precipitated formed which was collected and dried to obtained the product. NMR (300 MHz, DMSO-$d_6$) δ 10.0 (1H, s), 8.02 (1H, s), 7.94 (1H, d, J=7 Hz), 7.63 (1H, d, J=7 Hz), 7.52 (1H, t, J=7 Hz). 7.10 (3H, s), 4.83 (2H, s), 2.27 (3H, s), 2.07 (3H, s).

Step 2: Preparation of 3-azidomethyl-N-(2,3-dimethylphenyl)-benzamide (20)

To solution of 19 (1.0 g) in dimethylsulfoxide was added lithium azide (0.20 g). The resulting solution was stirred for 3 h, partitioned between ethyl acetate and water. The ethyl acetate layer was several times with water, saturated sodium chloride, dried over magnesium sulfate and concentrated in vacuo to obtain the product. NMR (300 MHz, DMSO-$d_6$) δ 10.0 (1H, s), 7.95 (2H, s), 7.55 (2h, m), 7.08 (3H, s), 4.55 (2H, s), 2.26 (3H, s), 2.07 (3H, s).

Step 3: Preparation of 3-aminomethyl-N-(2,3-dimethylphenyl)benzamide (21)

Starting with 20 (0.97 g) the method described in Step 2. of Example 1 was used to prepare the above named compound. NMR (300 MHz, DMSO-$d_6$) δ 9.91 (1H, s), 7.95 (1H, s), 7.83 (1H, d, J=8 Hz), 7.54 (1H, d, J=8 Hz), 7.45 (1H, t, J=8 Hz), 7.08 (3H, s,), 3.83 (2H, s), 3.34 (2H, b), 2.25 (3H, s), 2.07 (3H, s).

Step 4: Preparation of 3-[2(R)-(t-butyloxycarbonylamino)-3-(triphenylmethylmercapto)propylaminomethyl]-N-(2,3-dimethylphenyl)-benzamide (22)

Starting with 21 (0.13 g) the method described in Step 3. of Example 1 was used to prepare the above named compound. NMR (300 MHz, CDCl$_3$) δ 8.69 (1H, s), 8.31 (1H, s), 7.95 (1H, d, J=5 Hz), 7.50–7.16 (15H, m), 7.05 (3H, m), 5.05 (1H, m), 3.92 (2H, d), 2.78 (3H, m), 2.28 (3H, s), 2.20 (3H, s), 1.35 (9H, s).

Step 5: Preparation of 3-[2(R)-Amino-3-mercaptopropyl-aminomethyl]-N-(2, 3-dimethylphenyl)benzamide dihydrochloride (23)

Starting with 22 (0.35 g) the method described in Step 4. of Example 1 was used to prepare the above named compound. FAB mass spectrum m/e 344 (m+1).

Analysis Calculated for $C_{19}H_{25}N_3OS \cdot 2.6\ HCl \cdot 0.4\ H_2O$: C, 51.26; H, 6.43; N, 9.44; Found: C, 51.24; H, 6.41; N, 9.48.

EXAMPLE 19

3-[2(R)-Amino-3-mercaptopropylaminolbenzophenone trifluoroacetate (28).

Step 1: Preparation of Methyl 3-[2(R)-(t-butyloxycarbonyl-amino)-3-triphenylmethylmercaptopropyl-amino]benzoate (24)

Starting with methyl 3-aminobenzoate (0.61 g) the method described in Step 3. of Example 1 was used to prepare the above named compound. NMR (300 MHz, CDCl$_3$ ) δ 7.50–7.10 (18H, m), 6.70 (1H, d, J=8 Hz), 4.55 (1H, m), 3.88 (3H, s), 3.80 (1H, m), 3.08 (2H, m), 2.45 (3H, m), 1.43 (9H, s).

Step 2: Preparation of 3-[2(R)-(t-butyloxycarbonyl-amino)-3-(triphenylmethylmercapto)propylamino] benzoic acid (25)

To a solution of 24 (1.51 g) in methanol (70 mL) was added 5% sodium hydroxide (10 mL). The solution was stirred for 18 h, concentrated in vacuo, and the residue was partitioned between ethyl acetate and water. The ethyl acetate layer was extracted w/50 mL each of 2% potassium hydrogen sulfate, saturated sodium chloride, dried over magnesium sulfate and concentrated in vacuo to obtain the product. NMR (300 MHz, CDCl$_3$) δ 7.50–7.10 (18H, m), 6.76 (1H, m,), 4.60 (1H, m), 3.82 (1H, m), 3.08 (2H, m), 2.47 (3H, m), 1.43 (9H, s).

Step 3: Preparation of 3-[2(R)-(t-butyloxycarbonylamino)-3-(triphenylmethylmercapto)propylamino]-N-methoxy-N-methylbenzamide (26)

Starting with 25 (0.28 g) the method described in Step 1 of Example 1 was used to prepare the above named compound. NMR (300 MHz, CDCl$_3$) δ 7.50–7.20 (15H, m), 7.14 (1H, t, J=8 Hz), 6.92 (1H, d, J=8 Hz), 6.74 (1H, s), 6.60 (1H, d, J=8 Hz), 4.55 (1H, m), 3.58 (3H, s), 3.32 (3H, s), 3.08 (2H, m), 2.45 (3H, m), 1.43 (9H, s).

Step 4: Preparation of 3-[2(R)-(t-butyloxycarbonylamino)-3-(triphenyl-methylmercapto)propylamino]benzophenone (27)

To a solution of 26 (0.24 g) in tetrahydrofuran at 0° C. was added phenyl- magnesium chloride ( 0.78 mL/2M in THF). The solution was stirred for 18 h at 20° C. The reaction mixture was cooled again to 0° C., phenylmagnesium chloride ( 0.78 mL) was added and the solution was stirred for 18 h at 20° C. The reaction was quenched with water and partitioned with ethyl acetate. The ethyl acetate layer was extracted with 50 mL each of saturated sodium bicarbonate, saturated sodium chloride, dried over magnesium sulfate and concentrated in vacuo to obtain the crude product. Purification on silica gel with hexane/ethyl acetate 9/1 yielded the title compound.

Step 5: Preparation of 3-[2(R)-amino-3-mercaptopropylamino]-benzophenone trifluoroacetate (28)

Starting with 27 (0.21 g) the method described in Step 4. of Example 1 was used to prepare the above named compound. NMR (300 MHz, CD$_3$OD) δ 7.78 (1H, s), 7.75 (1H, d, J=3 Hz), 7.63 (1H, t, J=9 Hz), 7.51 (2H, t, J=9 Hz), 7.31

(1H, t, J=9 Hz), 7.11 (1H, t, J=3 Hz), 7.01 (2H, m), 3.52 (2H, m), 3.40 (1H, m), 2.87 (2H, dd). FAB mass spectrum m/e 287 (m+1).

Analysis Calculated for $C_{16}H_{18}N_2OS \cdot 1.3$ TFA$\cdot 0.7$ $H_2O$: C, 49.95; H, 4.67; N, 6.26; Found: C, 49.91; H, 5.54; N, 6.41.

EXAMPLE 20

3-[2(R)-Amino-3-mercaptopropylamino]-4-pentyl-N-(2,3-dimethylphenyl)-benzamide dihydrochloride (34)

Step 1: Preparation of methyl 3-nitro-4-(1-pentynyl) benzoate (29)

A solution of methyl 4-chloro-3-nitrobenzoate (0.70 g), bis(triphenylphosphine) palladium chloride (0.12 g), and 1-pentyne (2 mL) in triethylamine (12 mL) was placed in a sealed tube. The mixture was heated to 75° C. and stirred 18 h. The reaction mixture was cooled, filtered, and concentrated in vacuo. The resulting brown residue was chromatographed on silica gel with hexane/ethyl acetate 9/1 to obtain the product. NMR (300 MHz, $CDCl_3$) δ 8.61 (1H, d, J=2 Hz), 8.16 (1H, m), 7.64 (1H, m), 3.96 (3H, s), 2.49 (2H, t, J=7 Hz), 1.66 (2H, m, J=7 Hz), 1.06 (3H, t, J=7 Hz).

Step 2: Preparation of methyl 3-amino-4-pentylbenzoate (30)

Starting with 29 (0.32 g) the method described in Step 2 of Example 1 was used to prepare the above named compound. NMR (300 MHz, $CDCl_3$) δ 7.39 (1H, m), 7.34 (1H, d), 7.09 (1H, d), 3.87 (3H, s), 3.63 (2H, b), 2.50 (2H, t, J=8 Hz), 1.63 (2H, m), 1.35 (4H, m), 0.90 (3H, t, J=8 Hz).

Step 3: Preparation of Methyl 3-[2(R)-(t-butyloxycarbonylamino)-3-(triphenylmethylmercapto)propylamino]-4-pentylbenzoate (31)

Starting with 30 (0.24 g) the method described in Step 3. of Example 1 was used to prepare the above named compound. NMR (300 MHz, $CDCl_3$) δ 7.48–7.00 (18H, m), 3.87 (3H, s), 3.10 (2H, m), 2.48 (2H, m), 2.40 (1H, m), 1.43 (9H, s), 0.88 (3H, m).

Step 4: Preparation of 3-[2(R)-(t-butyloxycarbonylamino)-3-(triphenylmethylmercapto)propylamino]-4-pentylbenzoic acid (32)

Starting with 31 (0.37 g) the method described in Step 2. of Example 19 was used to prepare the above named compound. NMR (300 MHz, $CDCl_3$) δ 7.48–7.00 (18H, m), 3.08 (2H, m), 2.48 (2H, m), 2.40 (1H, m), 1.43 (9H, s), 0.88 (3H, m).

Step 5: Preparation of 3-[2(R)-(t-butyloxycarbonylamino)-3-(triphenylmethylmercapto)propylamino]-4-pentyl-N-(2,3-dimethylphenyl)benzamide Starting with 32 (0.31 g) the method described in Step 1. of Example 1 was used to prepare the above named compound. NMR (300 MHz, $CDCl_3$) δ 8.45 (1H, s), 8.10 (1H, d, J=8 Hz), 7.70–7.00 (19H, m), 2.28 (3H, s), 2.18 (3H, s), 1.29 (9H, s).

Step 6: Preparation of 3-[2(R)-Amino-3-mercaptopropylamino]-4-pentyl-N-(2,3-dimethylphenyl)benzamide dihydrochloride (34)

Starting with (33) (0.070 g) the method described in Step 4. of Example 1 was used to prepare the above named compound. FAB mass spectrum m/e 400 (m+1).

Analysis Calculated for $C_{23}H_{33}N_3OS \cdot 2.4$ HCl: C, 56.74; H, 7.33; N, 8.63; Found: C, 56.83; H, 7.05; N, 8.42.

EXAMPLE 21

3-[2(R)-Amino-3-mercaptopropylamino]-4-ethyl-N-(2,3-dimethylphenyl)-benzamide dihydrochloride (40)

Step 1: Preparation of methyl 4-acetyl-3-nitrobenzoate (35)

A solution of methyl 3-nitro-4-chlorobenzoate (0.70 g) in ethyl acetate (2 mL) was added to a solution of 1,8-diazabicyclo[5.4.0]undec-7-ene (1.50 mL) and nitroethane (0.70 mL) at 0° C. The mixture was stirred for 5 h and partitioned with ethyl acetate and water. Potassium permanganate (0.57 g) was added to the water layer and resulting solution was stirred for 45 minutes. Toluene (20 mL) was added and mixture was stirred slowly. The toluene layer was separated and washed with saturated sodium chloride, dried over magnesium sulfate and concentrated in vacuo to afford the crude product. Purification on silica gel with hexane/ethyl acetate 7/3 gave the title compound. NMR (300 MHz, $CDCl_3$) δ 8.74 (1H, s,), 8.36 (1H, d, J=8 Hz), 7.50 (1 H, d, J=8 Hz), 4.00 (3H, s), 2.58 (3H, s).

Step 2: Preparation of methyl 3-amino-4-ethylbenzoate (36)

The method described in Step 2. of Example 1 was applied to a solution of 35 (0.17 g) in methanol (20 mL) and 10% hydrochloric acid/water (5 mL) to prepare the above named compound. NMR (300 MHz, $CDCl_3$) δ 7.40 (1H, d, J=8 Hz), 7.34 (1H, s), 7.10 (1H, d, J=8 Hz), 3.88 (3H, s), 3.71 (2H, b), 2.54 (2H, q, J=8 Hz), 1.26 (3H, t, J=8 Hz).

Step 3: Preparation of methyl 3-[2(R)-(t-butyloxycarbonylamino)-3-(triphenylmethylmercapto)propylamino]-4-ethylbenzoate (37)

Starting with 36 (0.13 g) the method described in Step 3. of Example 1 was used to prepare the above named compound. NMR (300 MHz, $CDCl_3$) δ 7.50–7.05 (18H, m), 4.58 (1H, m), 3.92 (1H, m), 3.87 (3H, s), 3.10 (2H, m), 2.47 (3H, m), 2.42 (2H, q, J=8 Hz), 1.42 (9H, s), 1.19 (3H, t, J=8 Hz).

Step 4: Preparation of 3-[2(R)-(t-butyloxycarbonylamino)-3-(triphenylmethylmercapto)propylamino]-4-ethylbenzoic acid (38)

Starting with 37 (0.18 g) the method described in Step 2. of Example 19 was used to prepare the above named compound. NMR (300 MHz, $CDCl_3$) δ 7.50–7.05 (18H, m), 4.60 (1H, m), 3.92 (1H, m), 3.10 (2H, m), 2.47 (3H, m), 2.43 (2H, q, J=8 Hz), 1.42 (9H, s), 1.20 (3H, t, J=8 Hz).

Step 5: Preparation of 3-[2(R)-(t-butyloxycarbonylamino)-3-(triphenylmethyl-mercapto)propylamino]-4-ethyl-N-(2,3-dimethylphenyl)benzamide (39)

Starting with 38 (0.14 g) the method described in Step 1. of Example 1 was used to prepare the above named compound. NMR (300 MHz, CDCl$_3$) δ 8.44 (1H, s), 7.50–7.00 (17H, m), 4.65 (1H, m), 3.92 (1H, m), 3.18 (2H, m), 2.47 (3H, m), 2.40 (2H, q, J=8 Hz), 2.29 (3H, s), 2.18 (3H, s), 1.29 (9H, s), 1.21 (3H, t, J=8 Hz).

Step 6: Preparation of 3-[2(R)-Amino-3-mercaptopropylamino]-4-ethyl-N-(2,3-dimethylphenyl)-benzamide dihydrochloride (40)

Starting with (39) (0.090 g) the method described in Step 4. of Example 1 was used to prepare the above named compound. FAB mass spectrum m/e 358 (m+1).

Analysis Calculated for $C_{20}H_{27}N_3OS \cdot 2.3$ HCl·0.4 H$_2$O: C, 53.57; H, 6.77; N, 9.37; Found: C, 53.18; H, 6.59; N, 9.65.

EXAMPLE 22

N-[(2R)-2-Amino-3-mercaptopropyl]amino-3[(3-carboxyphenyl)oxy]benzene dihydrochloride (45)

Step 1: Preparation of 3-[(3-carbomethoxyphenyl)oxy]nitrobenzene (41)

A solution of methyl 3-iodobenzoate (2.54 g), 3-nitrophenol (1.48 g), and K$_2$CO$_3$ (3.97 g) in 60 mL of pyridine was warmed to 100° C. under nitrogen atmosphere. Copper powder (1.84 g) was added, and the reaction mixture was heated to reflux. After 22 h, The reaction was cooled to room temperature and poured into ethyl acetate and water. The organic layer was washed twice with 10% aq. HCl solution, then with sat. aq. NaHCO$_3$ solution, then with brine. The solution was dried (Na$_2$SO$_4$), filtered, and concentrated in vacuo to provide the crude product. Purification by silica gel chromatography (CH$_2$Cl$_2$) provided the product as a yellow oil.

Step 2: Preparation of 3-[(3-carbomethoxyphenyl)oxy]-aminobenzene (42)

To a solution of 41 (440 mg) in 30 mL of methanol under a nitrogen atmosphere was added 10% Pd/C (30 mg). The solution was purged with H$_2$ gas, then stirred at room temperature under a balloon atmosphere of H2. After 8 h, the reaction was flushed with nitrogen and filtered through celite to remove the catalyst, then concentrated in vacuo. The resulting brown oil was used without further purification.

Step 3: Preparation of N-[(2R)-(t-butoxycarbonylamino)-3-(triphenylmethyl-mercapto)propyl]amino-3-[(3-carbomethoxyphenyl)oxylbenzene 43)

To a solution of 42 (127 mg) in 6 mL of 1,2-dichloroethane at 0° C. was added 4A powdered molecular sieves (250 mg) and sodium triacetoxyborohydride (270 mg). N-t-butoxycarbonyl-S-(triphenylmethyl)cysteinal (259 mg) was added, followed by 2 drops of acetic acid. The cooling bath was removed, and the reaction was stirred for 24 hours. The reaction was poured into ethyl acetate and water. The organic layer was extracted with sat. aq. NaHCO$_3$ solution and brine, then dried (Na$_2$SO$_4$) and concentrated in vacuo to provide the product as a white foam.

Step 4: Preparation of N-[(2R)-(t-butoxycarbonylamino)-3-(triphenylmethyl-mercapto)propyl]amino-3-[(3-carboxyphenyl)oxy]benzene (44)

To a solution of 43 (0.52 mmol) in 8 mL of 3:1:1 methanol:THF:H$_2$O at room temperature was added solid NaOH (148 mg). After 2.5 h, the reaction was cooled to 0° C. and acidified to pH ~4 by dropwise addition of 10% aq. HCl solution. The solution was diluted with water and extracted three times with CH$_2$Cl$_2$. The combined organic layers were dried (Na$_2$SO$_4$) and concentrated in vacuo to provide the crude product. Purification by silica gel chromatography (3–8% MeOH/CH$_2$Cl$_2$) provided the titled compound as a pale yellow solid.

Step 5: N-[(2R)-2-Amino-3-mercaptopropyl]amino-3-[(3-carboxyphenyl)oxy]benzene dihydrochloride (45)

To a solution of 44 (201 mg) in 10 mL of CH$_2$Cl$_2$ was added triethylsilane (198 uL), followed by 5 mL of trifluoroacetic acid. The reaction was stirred for 30 minutes, then concentrated in vacuo, and partitioned with hexane and 2:1 water/MeOH. The water/MeOH solution was injected directly onto a Delta-Pak (C-18, 100A, 15 mm, 40 mm×100 mm) prep HPLC column. The gradient at 40 mL/min was 100% A (0.1% trifluoroacetic acid/water)for 5 min followed by 90% A to 45% A in 50 min (with B as 0.1% trifluoroacetic acid/acetonitrile). The pure fractions were pooled, concentrated in vacuo to near dryness, then taken up in 5 mL of water. This water solution was passed through a 2.0 g column of Bio-Rad AG 3-X4 chloride ion exchange resin with water rinses. The resulting aqueous column eluant was lyophilized 14 h to yield the titled compound as a solid.

FAB mass spectrum m/e 319 (M+1). Analysis calculated for $C_{16}H_{18}N_2O_3S \cdot 4.0$ HCl: C, 41.48; H, 4.79; N, 6.05; Found: C, 41.42; H, 4.79; N, 5.84.

Using the appropriate starting materials, the methods described above for Example 22 were used to prepare the following examples, except that in step 5, ion exchange prior to lyophilization was omitted.

EXAMPLE 23

N-[(2R)-2-Amino-3-mercaptopropyl]amino-3-[(4-carboxyphenyl)-oxy]benzene trifluoroacetate FAB mass spectrum m/e 319 (M+1). Analysis calculated for $C_{16}H_{18}N_2O_3S \cdot 1.70$ CF$_3$CO$_2$H: C, 45.49; H, 3.88; N, 5.47; Found: C, 45.53; H, 3.89; N, 5.37.

EXAMPLE 24

N-[(2R)-2-Amino-3-mercaptopropyl]amino-4-[(4-carboxyphenyl)-oxy]benzene bis(trifluoroacetate)

FAB mass spectrum m/e 319 (M+1). Analysis calculated for $C_{16}H_{18}N_2O_3S \cdot 2CF_3CO_2H \cdot 0.30$ H$_2$O: C, 43.53; H, 3.76; N, 5.08; Found: C, 43.54; H, 3.78; N, 5.08.

EXAMPLE 25

N-[(2R)-2-Amino-3-mercaptopropyl]amino-4-[(3-carboxyphenyl)-oxy]benzene bis(trifluoroacetate)

FAB mass spectrum m/e 319 (M+1). Analysis calculated for $C_{16}H_{18}N_2O_3S \cdot 2.75$ CF$_3$CO$_2$H: C, 40.86; H, 3.31; N, 4.43; Found: C, 40.90; H, 3.34; N, 4.40.

EXAMPLE 26

N-[(2R)-2-Amino-3-mercapto-1-oxopropyl]amino-
3-[(3-carboxyphenyl)oxy]benzene trifluoroacetate
(48)

Step 1: Preparation of N-[(2R)-(t-
butoxycarbonylamino)-1-oxo-3-(triphenylmethyl-
mercapto)propyl]amino-3 -[(3-carbomethoxyphenyl)
oxy]benzene (46)

To a solution of 42 (183 mg) [Example 22, Step 2] in 7 mL of dimethylformamide at room temperature was added N-t-butoxy-carbonyl-S-(triphenylmethyl)cysteine (404 mg), 1-hydroxybenzotriazole hydrate (181 mg), and 1-ethyl-3-(3-dimethylaminopropyl)carbodiimide hydrochloride (214 mg). After 14 h, the reaction was poured into ethyl acetate washed with sat. aq. $NH_4Cl$ solution, sat. aq. $NaHCO_3$ solution, water, and brine, then dried ($Na_2SO_4$) and concentrated in vacuo to provide the crude product. Purification by silica gel chromatography (0–5% MeOH/$CH_2Cl_2$) provided the product as a pale yellow foam.

Step 2: Preparation of N-[(2R)-(t-
butoxycarbonylamino)-1-oxo-3-(triphenylmethyl-
mercapto)propyl]amino-3-[(3-carboxyphenyl)oxy]
benzene (47)

The titled compound was prepared from 46 (175 mg) using the method in Step 4 of Example 22. The product was used in the next step without further purification.

Step 3: N-[(2R)-2-Amino-3-mercapto-1-oxopropyl]
amino-3-[(3-carboxyphenyl)oxy]benzene
trifluoroacetate (48)

The titled compound was prepared from 47 (139 mg) using the method in Step 5 of Example 22, except that ion exchange prior to lyophilization was omitted.

FAB mass spectrum m/e 333 (M+1). Analysis calculated for $C_{16}H_{18}N_2O_3S$•1.40 $CF_3CO_2H$•0.85 $H_2O$: C, 44.51; H, 3.79; N, 5.52; Found: C, 44.37; H, 3.40; N, 5.91.

Using the appropriate starting materials, the methods described above in Example 22, Steps 1 and 2, and Example 26 were employed to prepare the following examples.

EXAMPLE 27

N-[(2R)-2-Amino-3-mercapto-1-oxopropyl]amino-4-
[(3-carboxyphenyl)oxy]benzene trifluoroacetate FAB mass spectrum m/e 333 (M+1). Analysis calculated for $C_{16}H_{18}N_2O_3S$•1.15 $CF_3CO_2H$•0.15 $H_2O$: C, 47.15; H, 3.77; N, 6.01; Found: C, 47.16; H, 3.80; N, 5.74.

EXAMPLE 28

N-[(2R)-2-Amino-3-mercapto-1-oxopropyl]amino-4-
[(4-carboxyphenyl)oxy]benzene trifluoroacetate FAB mass spectrum m/e 333 (M+1). Analysis calculated for $C_{16}H_{18}N_2O_3S$•1.30 $CF_3CO_2H$•0.30 $H_2O$: C, 45.97; H, 3,71; N, 5.76; Found: C, 46.06; H, 3.68; N, 5.78.

Using the appropriate starting materials, the methods described above in Example 22, Steps 1 and 2, and Example 26 (except ester hydrolysis, Step 2) were employed to prepare the following examples.

EXAMPLE 29

N-[(2R)-2-Amino-3-mercapto-1-oxopropyl]amino-3-
[(3-carbomethoxyphenyl)oxy]benzene
trifluoroacetate FAB mass spectrum m/e 347 (M+1). Analysis calculated for $C_{16}H_{18}N_2O_3S$•1.60 $CF_3CO_2H$•0.10 $H_2O$ C, 45.72; H, 3.76; N, 5.28; Found: C, 45.70; H, 3.74; N, 5.42.

EXAMPLE 30

N-[(2R)-2-Amino-3-mercapto-1-oxopropyl]amino-4-
(3-carbomethoxyphenyl)oxy]benzene
trifluoroacetate FAB mass spectrum m/e 347 (M+1).

Analysis calculated for $C_{16}H_{18}N_2O_3S$•1.35 $CF_3CO_2H$: C, 47.29; H, 3.90; N, 5.60; Found: C, 47.31; H, 3.91; N, 5.62.

EXAMPLE 31

N-[(2R)-2-Amino-3-mercaptopropyl]amino-3[(3-
methylphenyl)oxy]-benzene hydrochloride (52)

Step 1: Preparation of 3-[(3-methylphenyl)oxy]
nitrobenzene (49)

To a solution of NaH (washed with hexane, 230 mg) in 7.0 mL of pyridine at 0° C. was added 3-nitrophenol (998 mg), and the solution was allowed to warm to room temperature. After 5 minutes, 3-iodotoluene (0.95 mL) was added, followed by CuBr•$SMe_2$ (1.75 g). The solution was heated to reflux under a stream of nitrogen. After 24 h, the reaction was cooled to room temperature and poured into ethyl acetate and water. The organic layer was washed twice with 10% aq. HCl solution, then with sat. aq. $NaHCO_3$ solution, then with brine. The solution was dried ($Na_2SO_4$), filtered, and concentrated in vacuo to provide the crude product.

Step 2: preparation of 3-[(3-methylphenyl)oxy]
aminobenzene (50)

To a solution of 49 (0.94 g) in 15 mL of methanol was added iron powder (1.05 g) and acetic acid (0.5 mL). The reaction was refluxed for 24 hours, then cooled to room temperature and poured into ethyl acetate and water. The organic layer was washed with water, sat. aq. $NaHCO_3$ solution, and brine. The solution was dried ($Na_2SO_4$), filtered, and concentrated in vacuo to provide the crude product. Purification by silica gel chromatography ($CH_2Cl_2$) provided the product as a pale yellow oil.

Step 3: Preparation of N-[(2R)-(t-
butoxycarbonylamino)-3-(triphenylmethyl-
mercapto)propyl]amino-3-[(3-methylphenyl)oxy]
benzene (51)

The above compound was prepared from 50 (171 mg) using the method in Step 3 of Example 22. The product was purified by silica gel chromatography (0–5% MeOH/$CH_2Cl_2$) to provide the product as a white foam.

Step 4: N-[(2R)-2-Amino-3-mercaptopropyl]
amino-3-[(3-methylphenyl)oxy]benzene
hydrochloride (52)

The titled compound was prepared from 51 (302 mg) using the method in Step 5 of Example 22.

FAB mass spectrum m/e 289 (M+1). Analysis calculated for $C_{16}H_{20}N_2OS$•1.0 HCl•0.10 $H_2O$: C, 58.83; H, 6.54; N, 8.58; Found: C, 58.84; H, 6.51; N, 8.55.

Using the appropriate starting materials, the methods described above in Example 31 were employed to prepare the following example.

EXAMPLE 32

N-[(2R)-2-Amino-3-mercaptopropyl]amino-3-(phenoxy)benzene hydrochloride

FAB mass spectrum m/e 275 (M+1). Analysis calculated for $C_{15}H_{18}N_2OS \cdot 1.70\ HCl \cdot 0.10\ H_2O$: C, 53.28; H, 5.93; N, 8.28; Found: C, 53.26; H, 5.57; N, 7.94.

EXAMPLE 33

N-[(2R)-2-Amino-3-mercaptopropyl]amino-4-(phenoxy)benzene hydrochloride (56)

Step 1: Preparation of 4-(phenoxy)nitrobenzene (53)

To a solution of 4-fluoronitrobenzene (0.50 mL) and phenol (443 mg) in 5.0 mL of dimethylformamide was added $K_2CO_3$ (1.27 g). The reaction was warmed to 70° C. for 20 h, then cooled to room temperature and poured into ethyl acetate and water. The organic layer was washed with water, sat. aq. $NaHCO_3$ solution, and brine. The solution was dried ($Na_2SO_4$), filtered, and concentrated in vacuo to provide the crude product as a yellow solid.

Step 2: Preparation of 4-(phenoxy)aminobenzene (54)

The titled compound was prepared from 53 (957 mg) using the method in Step 2 of Example 31.

Step 3: Preparation of N-[(2R)-(t-butoxycarbonylamino)-3-(triphenylmethylmercapto)propyl]amino-4-(phenoxy)benzene (55)

The titled compound was prepared from 54 (145 mg) using the method in Step 3 of Example 22. The product was isolated as a white foam, and used without further purification.

Step 4: N-[(2R)-2-Amino-3-mercaptopropyl]amino-3-[(3-methylphenyl)oxy]benzene hydrochloride (53)

The titled compound was prepared from 15 (513 rag) using the method in Step 5 of Example 22.

FAB mass spectrum m/e 275 (M+1). Analysis calculated for $C_{15}H_{18}N_2OS \cdot 1.60\ HCl \cdot 0.30\ H_2O$: C, 53.28; H, 6.02; N, 8.28; Found: C, 53.19; H, 5.99; N, 8.27.

Using the appropriate starting materials, the methods described above in Example 33 were employed to prepare the following examples.

EXAMPLE 34

N-[(2R)-2-Amino-3-mercaptopropyl]amino-4-[(3-methylphenyl)-oxy]benzene dihydrochloride FAB mass spectrum m/e 289 (M+1). Analysis calculated for $C_{16}H_{20}N_2OS \cdot 2.20\ HCl \cdot 0.30\ H_2O$: C, 51.38; H, 6.14; N, 7.49; Found: C, 51.48; H, 6.14; N, 7.48.

EXAMPLE 35

N-[(2R)-2-Amino-3-mercaptopropyl]amino-4-[(3-hydroxymethylphenyl)oxy]benzene hydrochloride FAB mass spectrum m/e 305 (M+1). Analysis calculated for $C_{16}H_{20}N_2O_2S \cdot 1.0\ HCl \cdot 0.30\ H_2O$: C, 55.50; H, 6.29; N, 8.09; Found: C, 55.60; H, 6.26; N, 7.89.

EXAMPLE 36

N-[(2R)-2-Amino-3-mercaptopropyl]amino-2-methyl-4-(phenoxy)benzene hydrochloride FAB mass spectrum m/e 289 (M+1). Analysis calculated for $C_{16}H_{20}N_2OS \cdot 0.90\ HCl \cdot 0.10\ H_2O$: C, 59.49; H, 6.58; N, 8.67; Found: C, 59.41; H, 6.53; N, 8.32.

EXAMPLE 37

[N-[(2R)-2-Amino-3-mercaptopropyl]amino-3-[2-(3-methylphenyl)-trans-ethenyl]benzene trifluoroacetate (59)

Step 1: Preparation of trans-3-[2-(3-methylphenyl) ethenyl]-aminobenzene (57)

A mixture of 3-bromoaniline (545 uL), 3-methylstyrene (780 uL), tri(o-tolyl)phosphine (60 mg), $Pd(OAc)_2$ (10 rag), and triethylamine (2.5 mL) was prepared in a sealed tube under argon atmosphere. The reaction was heated at 100° C. for 4 h, then cooled to room temperature and poured into ethyl acetate and water. The organic layer was washed with water and dried ($Na_2SO_4$), filtered, and concentrated in vacuo to provide the crude product. Purification by silica gel chromatography (20:1–5:1 hexane/EtOAc) provided the titled compound.

Step 2: Preparation of trans-N-[(2R)-(t-butoxycarbonylamino)-3-(triphenylmethyl-mercapto)propyl]amino-3-[2-(3-methylphenyl) ethenyl]aminobenzene (58)

The titled compound was prepared from 57 (210 mg) using the method described in Step 3 of Example 22.

Step 3: [N-[(2R)-2-Amino-3-mercaptopropyl] amino-3-[2-(3-methylphenyl)ethenyl]-trans-benzene trifluoroacetate (59)

The titled compound was prepared from 58 using the method described in Step 5 of Example 22, except that ion exchange prior to lyophilization was omitted.

Analysis calculated for $C_{18}H_{22}N_2S \cdot 1.10\ CF_3CO_2H$: C, 57.23; H, 5.49; N, 6.61; Found: C, 57.22; H, 5.55; N, 6.34.

EXAMPLE 38

N-[(2R)-2-Amino-3-mercaptopropyl]amino-3-[(1-naphthylmethyl)oxy]benzene dihydrochloride (63)

Step 1: Preparation of 3-[(1-naphthylmethyl)oxy] nitrobenzene (60)

To a solution of 3-nitrophenol (200 mg) in 4.0 mL of dimethylformamide at 0° C. was added NaH. After 10 minutes, 1-bromomethylnaphthalene (480 mg) was added, and the cold bath was removed. After ca. 15 h, the solution was quenched by the addition of sat. $NH_4Cl$ solution, and concentrated to dryness in vacuo. The residue was diluted with ethyl acetate and washed with water, sat. aq. $NaHCO_3$ solution, and brine. The solution was dried ($MgSO_4$), filtered, and concentrated in vacuo to provide the crude product. Trituration with 9:1 hexane/EtOAc provided the titled compound as a light brown solid.

Step 2: Preparation of 3-[(1-naphthylmethyl)oxy] aminobenzene (61)

The titled compound was prepared from 60 using the method described in Step 2 of Example 31.

Step 3: Preparation of N-[(2R)-(t-butoxycarbonylamino)-3-(triphenylmethylmercapto)propyl]amino-3-[(1-naphthylmethyl)oxy]benzene (62)

The titled compound was prepared from 62 using the method described in Step 3 of Example 22.

Step 4: N-[(2R)-2-Amino-3-mercaptopropyl]amino-3-[(1-naphthylmethyl)oxy]benzene dihydrochloride (63)

The titled compound was prepared from 62 using the method in Step 5 of Example 22.

FAB mass spectrum m/e 339 (M+1). Analysis calculated for $C_{20}H_{22}N_2OS \cdot 2\ HCl \cdot 0.70\ H_2O$: C, 56.66; H, 5.88; N, 6.81; Found: C, 56.56; H, 6.13; N, 6.84.

Using the appropriate starting materials, the methods described above in Example 38 were employed to prepare the following example, except that ion exchange prior to lyophilization of the final product was omitted.

EXAMPLE 39

N-[(2R)-2-Amino-3-mercaptopropyl]amino-2-(benzyloxy)benzene trifluoroacetate

Analysis calculated for $C_{16}H_{20}N_2OS \cdot 1.40\ CF_3CO_2H \cdot 0.02\ H_2O$: C, 50.36; H, 4.82; N, 6.25; Found: C, 50.37; H, 4.77; N, 6.60.

Using commercially avaliable 2-phenoxyaniline, the methods described above in Example 22 Steps 3 and 5 were employed to prepare the following example.

EXAMPLE 40

N-[(2R)-2-Amino-3-mercaptopropyl]amino-2-(phenoxy)benzene hydrochloride

Analysis calculated for $C_{15}H_{18}N_2OS \cdot 1.56\ HCl \cdot 0.02\ H_2O$: C, 54.33; H, 5.96; N, 8.45; Found: C, 54.35; H, 5.86; N, 8.36.

EXAMPLE 41

2-[2(R)-Amino-3-mercaptopropylamino]-N-(3-methylphenyl)-benzamide trifluoroacetate (65)

Step 1: Preparation of 2-amino-N-(3-methylphenyl)benzamide (64)

To a solution of 2-aminobenzoic acid (290 mg) and 3-methylaniline (215 mg) in 10 mL of DMF was added 1-hydroxybenzotriazole (300 mg), EDC (400 mg) and triethylamine (500 µL). The resulting solution was stirred for 16 h. The reaction solution was partitioned with ethyl acetate and water. The ethyl acetate layer was extracted w/50 mL each of 5% citric acid, saturated sodium bicarbonate, saturated sodium chloride, dried over magnesium sulfate and concentrated in vacuo to afford the title compound as a solid.

Step: Preparation of 2-[2(R)-Amino-3-mercaptopropylamino]-N-(3-methylphenyl)-benzamide trifluoroacetate (65)

The title compound was prepared from 64 using the method described in Steps 3 and 4 of Example 1, except that the ion exchange with BioRad AG 3-X4 was omitted.

Analysis Calculated for $C_{17}H_{21}N_3OS \cdot 1.15\ TFA \cdot 0.3\ H_2O$: C, 51.28; H, 5.07; N, 9.30; Found: C, 51.29; H, 5.04; N, 9.29.

EXAMPLE 42

In vitro inhibition of ras farnesyl transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS* U.S.A. 86:6630–6634 (1989), respectively. Bovine FPTase was assayed in a volume of 100 µl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 µg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 µM ZnCl$_2$ and 100 nM Ras-CVIM were added to the reaction mixture. Reactions were performed for 30 min., stopped with 100 µl of 30% (v/v) trichloroacetic acid (TCA) in ethanol and processed as described above for the bovine enzyme.

The compounds of the instant invention, and those compounds not of the invention, described in the Examples were tested for inhibitory activity against human FPTase by the assay described above and were found to have IC$_{50}$ of <50 µM.

EXAMPLE 43

In vivo ras farnesylation assay

The cell line used in this assay is a v-ras line derived from either Rat1 or NIH3T3 cells, which expressed viral Ha-ras p21. The assay is performed essentially as described in DeClue, J.E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000 x g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X100.0.5% deoxycholate/0.1%/SDS/ 0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

EXAMPLE 44

In vivo growth inhibition assay

To determine the biological consequences of FPTase inhibition, the effect of the compounds of the instant invention on the anchorage-independent growth of Rail cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1 \times 10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase of the formula A:

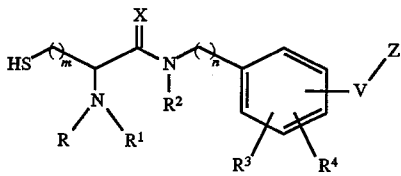

A wherein:
X is O or $H_2$;
m is 1 or 2;
n is 0 or 1;
q is 0, 1 or 2;
t is 1 to 4;
R, $R^1$ and $R^2$ are independently selected from: H, $C_{1-6}$ alkyl, or $C_{1-6}$ aralkyl;
$R^3$ and $R^4$ are independently selected from:
  a) hydrogen,
  b) $C_1-C_6$ alkyl,
  c) $C_1-C_6$ alkyl substituted by $C_2-C_6$ alkenyl, $R^6O$—, $R^5S(O)_q$—, $R^7C(O)NR^6$—, CN, $N_3$, $R^6OC(O)NR^6$—, $R^6R^7N$—$C(NR^6R^8)$—, $R^6C(O)$—, $R^7R^8NC(O)O$—, $R^7R^8NC(O)$—, $R^6R^7N$—$S(O)_2$—, —$NR^6S(O)_2R^5$, $R^6OC(O)O$—, —$NR^6R^7$, or $R^7R^8NC(O)NR^6$—,
  d) substituted cycloalkyl,
  e) cycloalkyl, alkenyl, $R^6O$—, $R^5S(O)_q$—, $R^6C(O)NR^6$—, CN, $NO_2$, $R^6R^7N$—$C(NR^8)$—, $R^6C(O)$—, $N_3$, —$NR^6R^7$, halogen or $R^7OC(O)NR^6$—, and
  f) $C_1-C_6$ alkyl substituted with a group selected from: aryl, substituted aryl, heterocyclic, substituted heterocyclic, $C_3-C_{10}$ cycloalkyl and substituted $C_3-C_{10}$ cycloalkyl;

Z is unsubstituted or substituted $C_{1-8}$ alkyl, unsubstituted or substituted $C_{2-8}$ alkenyl, unsubstituted or substituted aryl, unsubstituted or substituted heterocycle;

wherein the substituted $C_{1-8}$ alkyl, substituted $C_{2-8}$ alkenyl, substituted aryl or substituted heterocycle is substituted with one or more substituents selected from:
  1) $C_{1-4}$ alkyl,
  2) $C_{1-4}$ alkyl substituted with:
    a) $C_{1-4}$ alkoxy,
    b) $NR^6R^7$,
    c) $C_{3-6}$ cycloalkyl,
    d) aryl or heterocycle,
    e) HO,
  3) aryl or heterocycle,
  4) halogen,
  5) $OR^6$,
  6) $NR^6R^7$,
  7) CN,
  8) $NO_2$, or
  9) $CF_3$;

$R^5$ is $C_{1-4}$ alkyl or aralkyl;
$R^6$, $R^7$ and $R^8$ are independently selected from: H, $C_{1-4}$ alkyl, substituted $C_{1-4}$ alkyl, $C_{3-6}$ cycloalkyl, substituted $C_{3-6}$ cycloalkyl, heterocycle, substituted heterocycle, aryl, substituted aryl, aroyl, substituted aroyl, heteroaroyl, substituted heteroaroyl, arylsulfonyl, substituted arylsulfonyl, heteroarylsulfonyl or substituted heteroarylsulfonyl, wherein the substituted $C_{1-4}$ alkyl, substituted $C_{3-6}$ cycloalkyl, substituted heterocycle, substituted aryl, substituted aroyl, substituted heteroaroyl, substituted arylsulfonyl or substituted heteroarylsulfonyl is substituted with one or more substituents selected from:
  a) $C_{1-4}$ alkoxy,
  b) aryl or heterocycle,
  c) halogen,
  d) HO,
  e) 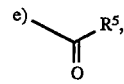
  f) —$SO_2R^5$, or
  g) —$NR^6R^7$, or $R^6$ and $R^7$ may be joined in a ring, and
$R^7$ and $R^8$ may be joined in a ring;
$R^9$ is selected from: H, $C_{1-4}$ alkyl, substituted $C_{1-4}$ alkyl, $C_{3-6}$ cycloalkyl, substituted $C_{3-6}$ cycloalkyl, heterocycle, substituted heterocycle, aryl and substituted aryl, wherein the substituted $C_{1-4}$ alkyl, substituted $C_{3-6}$ cycloalkyl, substituted heterocycle or substituted aryl is substituted with one or two substituents independently selected from:
  a) $C_{1-4}$ alkyl,
  b) $C_{1-4}$ alkoxy,
  c) aryl or heterocycle,
  d) halogen, e) HO,

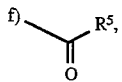

g) —SO₂R⁵, and h) —NR⁶R⁷;

V is selected from: —C(R¹¹)=C(R¹¹)—, —C≡C—, —C(O)—, —C(R¹¹)₂—, —C(OR¹¹)R¹¹—, —CN(R¹¹)₂R¹¹—, —OC(R¹¹)₂—, —NR¹¹C(R¹¹)₂—, —C(R¹¹)₂O—, —C(R¹¹)₂NR¹¹—, —C(O)NR¹¹—, —NR¹¹C(O)—, O, —NC(O)R¹¹—, —NC(O)OR¹¹—, —S(O)₂N(R¹¹)—, —N(R¹¹)S(O)₂—, or S(O)ₘ;

R¹⁰ and R¹¹ are independently selected from hydrogen, C₁–C₆ alkyl, C₂–C₄ alkenyl, benzyl and aryl; or a disulfide or pharmaceutically acceptable salt thereof.

2. A compound which inhibits farnesyl-protein transferase of the formula B:

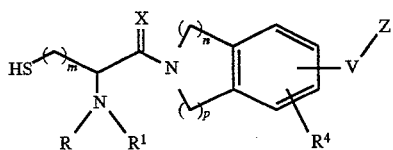

wherein:

X is O or H₂;

m is 1 or 2;

n is 0 or 1;

p is 1, 2 or 3;

q is 0, 1 or 2;

t is 1 to 4;

R and R¹ are independently selected from: H, C₁–₆ alkyl, or C₁–₆ aralkyl;

R⁴ is independently selected from:

a) hydrogen, b) C₁–C₆ alkyl, c) C₁–C₆ alkyl substituted by C₂–C₆ alkenyl, R⁶O—, R⁵S(O)_q—, R⁷C(O)NR⁶—, CN, N₃, R⁶OC(O)NR⁶—, R⁶R⁷N—C(NR⁶R⁸)—, R⁶C(O)—, R⁷R⁸NC(O)O—, R⁷R⁸NC(O)—, R⁶R⁷N—S(O)₂—, —NR⁶S(O)₂R⁵, R⁶OC(O)O—, —NR⁶R⁷, or R⁷R⁸NC(O)NR⁶—, d) substituted cycloalkyl, e) cycloalkyl, alkenyl, R⁶O—, R⁵S(O)_q—, R⁶C(O)NR⁶—, CN, NO₂, R⁶R⁷N—C(NR⁸)—, R⁶C(O)—, N₃, —NR⁶R⁷, halogen or R⁷OC(O)NR⁶—, and f) C₁–C₆ alkyl substituted with a group selected from: aryl, substituted aryl, heterocyclic, substituted heterocyclic, C₃–C₁₀ cycloalkyl and substituted C₃–C₁₀ cycloalkyl;

Z is unsubstituted or substituted C₁–₈ alkyl, unsubstituted or substituted C₂–₈ alkenyl, unsubstituted or substituted aryl, unsubstituted or substituted heterocycle;

wherein the substituted C₁–₈ alkyl, substituted C₂–₈ alkenyl, substituted aryl or substituted heterocycle is substituted with one or more substituents selected from:

1) C₁–₄ alkyl,

2) C₁–₄ alkyl substituted with:

a) C₁–₄ alkoxy, b) NR⁶R⁷, c) C₃–₆ cycloalkyl, d) aryl or heterocycle, e) HO, 3) aryl or heterocycle, 4) halogen,

5) OR⁶,

6) NR⁶R⁷,

7) CN,

8) NO₂, or

9) CF₃;

R⁵ is C₁–₄ alkyl or aralkyl;

R⁶, R⁷ and R⁸ are independently selected from: H, C₁–₄ alkyl, substituted C₁–₄ alkyl, C₃–₆ cycloalkyl, substituted C₃–₆ cycloalkyl, heterocycle, substituted heterocycle, aryl, substituted aryl, aroyl, substituted aroyl, heteroaroyl, substituted heteroaroyl, arylsulfonyl, substituted arylsulfonyl, heteroarylsulfonyl or substituted heteroarylsulfonyl, wherein the substituted C₁–₄ alkyl, substituted C₃–₆ cycloalkyl, substituted heterocycle, substituted aryl, substituted aroyl, substituted heteroaroyl, substituted arylsulfonyl or substituted heteroarylsulfonyl is substituted with one or more substituents selected from:

a) C₁–₄ alkoxy, b) aryl or heterocycle, c) halogen, d) HO,

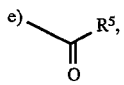

f) —SO₂R⁵, or g) —NR⁶R⁷, or

R⁶ and R⁷ may be joined in a ring, and

R⁷ and R⁸ may be joined in a ring;

R⁹ is selected from: H, C₁–₄ alkyl, substituted C₁–₄ alkyl, C₃–₆ cycloalkyl, substituted C₃–₆ cycloalkyl, heterocycle, substituted heterocycle, aryl and substituted aryl, wherein the substituted C₁–₄ alkyl, substituted C₃–₆ cycloalkyl, substituted heterocycle or substituted aryl is substituted with one or two substituents independently selected from:

a) C₁–₄ alkyl, b) C₁–₄ alkoxy, c) aryl or heterocycle, d) halogen, e) HO,

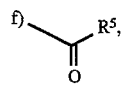

g) —SO₂R⁵, and h) —NR⁶R⁷;

V is selected from: —CH=CH—, —C≡C—, —C(O)—, —C(R¹¹)₂—, —C(OR¹¹)R¹¹—, —CN(R¹¹)₂R¹¹—, —OC(R¹¹)₂—, —NR¹¹C(R¹¹)₂—, —C(R¹¹)₂O—, —C(R¹¹)—₂NR¹¹—, —C(O)NR¹¹—, —NR¹¹C(O)—, O, —NC(O)R¹¹—, —NC(O)OR¹¹—, —S(O)₂N(R¹¹)—, —N(R¹¹)S(O)₂—, or S(O)ₘ;

R¹⁰ and R¹¹ are independently selected from hydrogen, C₁–C₆ alkyl, C₂–C₄ alkenyl, benzyl and aryl;

or a disulfide or pharmaceutically acceptable salt thereof.

3. A compound which inhibits farnesyl-protein transferase of the formula C:

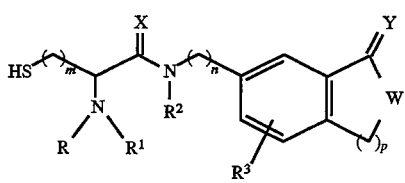

wherein:
X and Y are independently O or $H_2$;
m is 1 or 2;
n is 0 or 1;
p is 1, 2 or 3;
q is 0, 1 or 2;
t is 1 to 4;
R, $R^1$ and $R^2$ are independently selected from: H, $C_{1-6}$ alkyl, or $C_{1-6}$ aralkyl;
$R^3$ is independently selected from:
 a) hydrogen,
 b) $C_1$–$C_6$ alkyl,
 c) $C_1$–$C_6$ alkyl substituted by $C_2$–$C_6$ alkenyl, $R^6O$—, $R^5S(O)_q$—, $R^7C(O)NR^6$—, CN, $N_3$, $R^6OC(O)NR^6$—, $R^6R^7N$—$C(NR^6R^8)$—, $R^6C(O)$—, $R^7R^8NC(O)O$—, $R^7R^8NC(O)$—, $R^6R^7N$—$S(O)_2$—, —$NR^6S(O)_2R^5$, $R^6OC(O)O$—, —$NR^6R^7$, or $R^7R^8NC(O)NR^6$—,
 d) substituted cycloalkyl,
 e) cycloalkyl, alkenyl, $R^6O$—, $R^5S(O)_q$—, $R^6C(O)NR^6$—, CN, $NO_2$, $R^6R^7N$—$C(NR^8)$—, $R^6C(O)$—, $N_3$, —$NR^6R^7$, halogen or $R^7OC(O)NR^6$—, and
 f) $C_1$–$C_6$ alkyl substituted with a group selected from: aryl, substituted aryl, heterocyclic, substituted heterocyclic, $C_3$–$C_{10}$ cycloalkyl and substituted $C_3$–$C_{10}$ cycloalkyl;
W is —$CHR^9$— or —$NR^9$—;
$R^5$ is $C_{1-4}$ alkyl or aralkyl;
$R^6$, $R^7$ and $R^8$ are independently selected from: H, $C_{1-4}$ alkyl, substituted $C_{1-4}$ alkyl, $C_{3-6}$ cycloalkyl, substituted $C_{3-6}$ cycloalkyl, heterocycle, substituted heterocycle, aryl, substituted aryl, aroyl, substituted aroyl, heteroaroyl, substituted heteroaroyl, arylsulfonyl, substituted arylsulfonyl, heteroarylsulfonyl or substituted heteroarylsulfonyl,
wherein the substituted $C_{1-4}$ alkyl, substituted $C_{3-6}$ cycloalkyl, substituted heterocycle, substituted aryl, substituted aroyl, substituted heteroaroyl, substituted arylsulfonyl or substituted heteroarylsulfonyl is substituted with one or more substituents selected from:
 a) $C_{1-4}$ alkoxy,
 b) aryl or heterocycle,
 c) halogen,
 d) HO,

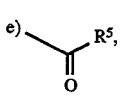

f) —$SO_2R^5$, or
 g) —$NR^6R^7$, or
$R^6$ and $R^7$ may be joined in a ring, and
$R^7$ and $R^8$ may be joined in a ring;
$R^9$ is selected from: H, $C_{1-4}$ alkyl, substituted $C_{1-4}$ alkyl, $C_{3-6}$ cycloalkyl, substituted $C_{3-6}$ cycloalkyl, heterocycle, substituted heterocycle, aryl and substituted aryl,
wherein the substituted $C_{1-4}$ alkyl, substituted $C_{3-6}$ cycloalkyl, substituted heterocycle or substituted aryl is substituted with one or two substituents independently selected from:

a) $C_{1-4}$ alkyl,
 b) $C_{1-4}$ alkoxy,
 c) aryl or heterocycle,
 d) halogen,
 e) HO,

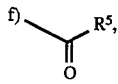

g) —$SO_2R^5$, and
 h) —$NR^6R^7$; or a disulfide or pharmaceutically acceptable salt thereof.

4. A compound which inhibits farnesyl-protein transferase of the formula D:

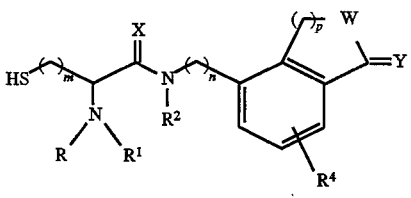

wherein:
X and Y are independently O or $H_2$;
m is 1 or 2;
n is 0 or 1;
p is 1, 2 or 3;
q is 0, 1 or 2;
t is 1 to 4;
R, $R_1$ and $R_2$ are independently selected from: H, $C_{1-6}$ alkyl, or $C_{1-6}$ aralkyl;
$R^4$ is independently selected from:
 a) hydrogen,
 b) $C_1$–$C_6$ alkyl,
 c) $C_1$–$C_6$ alkyl substituted by $C_2$–$C_6$ alkenyl, $R^6O$—, $R^5S(O)_q$—, $R^7C(O)NR^6$—, CN, $N_3$, $R^6OC(O)NR^6$—, $R^6R^7N$-$C(NR^6R^8)$—, $R^6C(O)$—, $R^7R^8NC(O)O$—, $R^7R^8NC(O)$—, $R^6R^7N$—$S(O)_2$—, —$NR^6S(O)_2R^5$, $R^6OC(O)O$—, —$NR^6R^7$, or $R^7R^8NC(O)NR^6$—,
 d) substituted cycloalkyl,
 e) cycloalkyl, alkenyl, $R^6O$—, $R^5S(O)_q$—, $R^6C(O)NR^6$—, CN, $NO_2$, $R^6R^7N$—$C(NR^8)$—, $R^6C(O)$—, $N_3$, —$NR^6R^7$, halogen or $R^7OC(O)NR^6$—, and
 f) $C_1$–$C_6$ alkyl substituted with a group selected from: aryl, substituted aryl, heterocyclic, substituted heterocyclic, $C_3$–$C_{10}$ cycloalkyl and substituted $C_3$–$C_{10}$ cycloalkyl;
W is —$CHR^9$— or —$NR^9$—;
$R^5$ is $C_{1-4}$ alkyl or aralkyl;
$R^6$, $R^7$ and $R^8$ are independently selected from: H, $C_{1-4}$ alkyl, substituted $C_{1-4}$ alkyl, $C_{3-6}$ cycloalkyl, substituted $C_{3-6}$ cycloalkyl, heterocycle, substituted heterocycle, aryl, substituted aryl, aroyl, substituted aroyl, heteroaroyl, substituted heteroaroyl, arylsulfonyl, substituted arylsulfonyl, heteroarylsulfonyl or substituted heteroarylsulfonyl,
wherein the substituted $C_{1-4}$ alkyl, substituted $C_{3-6}$ cycloalkyl, substituted heterocycle, substituted aryl, substituted aroyl, substituted heteroaroyl, substituted arylsulfonyl or substituted heteroarylsulfonyl is substituted with one or more substituents selected from:
 a) $C_{1-4}$ alkoxy,
 b) aryl or heterocycle, c) halogen,
d) HO, e) 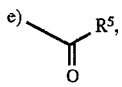

f) —SO$_2$R$^5$, or
g) —NR$^6$R$^7$, or
R$^6$ and R$^7$ may be joined in a ring, and
R$^7$ and R$^8$ may be joined in a ring;
R$^9$ is selected from: H, C$_{1-4}$ alkyl, substituted C$_{1-4}$ alkyl, C$_{3-6}$ cycloalkyl, substituted C$_{3-6}$ cycloalkyl, heterocycle, substituted heterocycle, aryl and substituted aryl,
wherein the substituted C$_{1-4}$ alkyl, substituted C$_{3-6}$ cycloalkyl, substituted heterocycle or substituted aryl is substituted with one or two substituents independently selected from:

a) C$_{1-4}$ alkyl,
b) C$_{1-4}$ alkoxy,
c) aryl or heterocycle,
d) halogen,
e) HO, f) 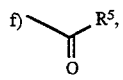

g) —SO$_2$R$^5$, and
h) —NR$^6$R$^7$;

or a disulfide or pharmaceutically acceptable salt thereof.

5. The compound according to claim 1 of the formula A:

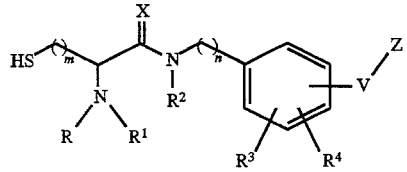

A wherein:
X is H$_2$;
m is 1;
n is or 0 or 1;
R, R$^1$ and R$^2$ are independently selected from: H, C$_{1-6}$ alkyl, or C$_{1-6}$ aralkyl;
R$^3$ and R$^4$ are independently selected from: H, C$_{1-8}$ alkyl, aryl, —SO$_2$R$^5$, —OR$^6$,
Z is unsubstituted or substituted C$_{1-8}$ alkyl, unsubstituted or substituted aryl, unsubstituted or substituted heterocycle;
wherein the substituted C$_{1-8}$ alkyl, substituted aryl or substituted heterocycle is substituted with one or more substituents selected from:
1) C$_{1-4}$ alkyl,
2) C$_{1-4}$ alkyl substituted with:
a) C$_{1-4}$ alkoxy,
b) NR$^6$R$^7$,
c) C$_{3-6}$ cycloalkyl,
d) aryl or heterocycle,
e) HO,
3) aryl or heterocycle,
4) halogen,
5) OR$^6$,
6) NR$^6$R$^7$,
7) CN,
8) NO$_2$, or
9) CF$_3$;

R$^5$ is C$_{1-4}$ alkyl or aralkyl;
R$^6$ and R$^7$ are independently selected from: H, C$_{1-4}$ alkyl, substituted C$_{1-4}$ alkyl, C$_{3-6}$ cycloalkyl, substituted C$_{3-6}$ cycloalkyl, heterocycle, substituted heterocycle, aryl, substituted aryl, aroyl, substituted aroyl, heteroaroyl, substituted heteroaroyl, arylsulfonyl, substituted arylsulfonyl, heteroarylsulfonyl or substituted heteroarylsulfonyl,
wherein the substituted C$_{1-4}$ alkyl, substituted C$_{3-6}$ cycloalkyl, substituted heterocycle, substituted aryl, substituted aroyl, substituted heteroaroyl, substituted arylsulfonyl or substituted heteroarylsulfonyl is substituted with one or more substituents selected from:
a) C$_{1-4}$ alkoxy,
b) aryl or heterocycle,
c) halogen,
d) HO, e) 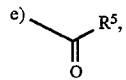

f) —SO$_2$R$^5$, or
g) —NR$^6$R$^7$, or
R$^6$ and R$^7$ may be joined in a ring, and
V is selected from: —CH=CH—, —C≡C—, —C(O)—, —C(R$^{11}$)$_2$—, —C(OR$^{11}$)R$^{11}$—, —CN(R$^{11}$)$_2$R$^{11}$—, —OC(R$^{11}$)$_2$—, —NR$^{11}$C(R$^{11}$)$_2$—, —C(R$^{11}$)$_2$O—, —C(R$^{11}$)$_2$NR$^{11}$—, —C(O)NR$^{11}$—, —NR$^{11}$C(O)—, O, —NC(O)R$^{11}$—, —NC(O)OR$^{11}$—, —S(O)$_2$N(R$^{11}$)—, —N(R$^{11}$)S(O)$_2$—, or S(O)$_m$;

R$^{10}$ and R$^{11}$ are independently selected from hydrogen, C$_1$-C$_6$ alkyl, C$_2$-C$_4$ alkenyl, benzyl and aryl;
or a disulfide or pharmaceutically acceptable salt thereof.

6. The compound according to claim 4 of the formula D:

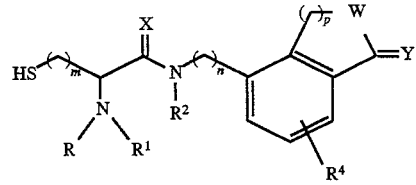

D wherein:
X is H$_2$;
Y is O;
m is 1;
n is 0 or 1;
p is 1, 2 or 3;
t is 1 to 4;
R, R$^1$ and R$^2$ are independently selected from: H, C$_{1-6}$ alkyl, or C$_{1-6}$ aralkyl;
R$^4$ is selected from: H; C$_{1-8}$ alkyl, aryl, —SO$_2$R$^5$, —OR$^6$,
W is —NR$^9$—;
R$^5$ is C$_{1-4}$ alkyl or aralkyl;
R$^6$ and R$^7$ are independently selected from: H, C$_{1-4}$ alkyl, substituted C$_{1-4}$ alkyl, C$_{3-6}$ cycloalkyl, substituted C$_{3-6}$ cycloalkyl, heterocycle, substituted heterocycle, aryl, substituted aryl, aroyl, substituted aroyl, heteroaroyl, substituted heteroaroyl, arylsulfonyl, substituted arylsulfonyl, heteroarylsulfonyl or substituted heteroarylsulfonyl,
wherein the substituted C$_{1-4}$ alkyl, substituted C$_{3-6}$ cycloalkyl, substituted heterocycle, substituted aryl, substituted aroyl, substituted heteroaroyl, substituted arylsulfonyl or substituted heteroarylsulfonyl is substituted with one or more substituents selected from:

a) $C_{1-4}$ alkoxy,
b) aryl or heterocycle,
c) halogen,
e) HO,

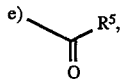

g) —$SO_2R^5$, or
h) —$NR^6R^7$, or
$R^6$ and $R^7$ may be joined in a ring;
$R^9$ is selected from: H, $C_{1-4}$ alkyl, substituted $C_{1-4}$ alkyl, aryl and substituted aryl,
wherein the substituted $C_{1-4}$ alkyl or substituted aryl is substituted with one or two substituents independently selected from:

a) $C_{1-4}$ alkyl,
b) $C_{1-4}$ alkoxy,
c) aryl or heterocycle,
d) halogen,
e) HO,

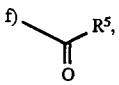

g) —$SO_2R^5$, and
h) —$NR^6R^7$;

or a disulfide or pharmaceutically acceptable salt thereof.

7. A compound which inhibits farnesyl-protein transferase which is:

3-[2(R)-Amino-3-mercaptopropylamino]-N-(2,3-dimethylphenyl)-benzamide
3-[2(R)-Amino-3-mercaptopropylamino]-N-phenyl-N-methylbenzamide
3-[2(R)-Amino-3-mercaptopropylamino]-N-(1-naphthylmethyl)-benzamide
3-[2(R)-Amino-3-mercaptopropylamino]-N-phenylbenzamide
3-[2(R)-Amino-3-mercaptopropylamino]-N-benzylbenzamide
3-[2(S)-Amino-3-mercaptopropylamino]-N-(2,3-dimethylphenyl)-benzamide
3-[2(R)-Amino-3-mercaptopropanoylamino]-N-(2,3-dimethylphenyl)-benzamide
3-[2(R)-Amino-3-mercaptopropylamino]-4-methyl-N-(2,3-dimethylphenyl)-benzamide
3-[2(R)-Amino-3-mercaptopropylamino]-4-methoxy-N-(2,3-dimethylphenyl)-benzamide
3-[2(R)-Amino-3-mercaptopropylamino]-6-methyl-N-(2,3-dimethylphenyl)-benzamide
3-[2(R)-Amino-3-mercaptopropylamino]-N-[1-(5,6,7,8-tetrahydronaphthyl)]-benzamide
1-[3-[2(R)-Amino-3-mercaptopropylamino]phenylcarbonyl]indoline
1-[2(R)-Amino-3-mercaptopropylamino]-3-[(2,3-dimethylbenzoyl)amino]-benzene
4-[2(R)-Amino-3-mercaptopropylamino]-2-(2,3-dimethylphenyl)-isoindolin-1-one
4-[2(R)-Amino-3-mercaptopropylamino]-2-benzylisoindolin-1-one
1-[2(R)-Amino-3-mercaptopropylamino]-N-(2,3-dimethylphenyl)-4-indoline carboxamide
1-[2(R)-Amino-3-mercaptopropylamino]-3-[(2,3-dimethylphenyl)-aminomethyl]-benzene
3-[2(R)-Amino-3-mercaptopropylaminomethyl]-N-(2,3-dimethylphenyl)-benzamide
3-[2(R)-Amino-3-mercaptopropylamino]benzophenone
3-[2(R)-Amino-3-mercaptopropylamino]-4-pentyl-N-(2,3-dimethylphenyl)-benzamide
3-[2(R)-Amino-3-mercaptopropylamino]-4-ethyl-N-(2,3-dimethylphenyl)-benzamide
N-[(2R)-2-amino-3-mercaptopropyl]amino-3-[2-(3-methylphenyl)-trans-ethenyl]benzene
N-[(2R)-2-amino-3-mercaptopropyl]amino-3-[(1-naphthylmethyl)oxy]benzene
N-[(2R)-2-amino-3-mercaptopropyl]amino-2-(phenoxy)benzene
N-[(2R)-2-amino-3-mercaptopropyl]amino-2-(benzyloxy)benzene
N-[(2R)-2-amino-3-mercaptopropyl]amino-4-(phenoxy)benzene
N-[(2R)-2-amino-3-mercaptopropyl]amino-4-[(3-methylphenyl)oxy]benzene
N-[(2R)-2-amino-3-mercaptopropyl]amino-3-(phenoxy)benzene
N-[(2R)-2-amino-3-mercaptopropyl]amino-3-[(3-methylphenyl)oxy]benzene
N-[(2R)-2-amino-3-mercaptopropyl]amino-4-[(3-(hydroxymethyl)phenyl)oxy]benzene
N-[(2R)-2-amino-3-mercaptopropyl]amino-2-methyl-4-(phenoxy)benzene or
2-[2(R)-amino-3-mercaptopropylamino]-N-(3-methylphenyl)-benzamide or a disulfide or pharmaceutically acceptable salt thereof.

8. The compound of claim 7 which is:

3-[2(S)-Amino-3-mercaptopropylamino]-N-(2,3-dimethylphenyl)-benzamide

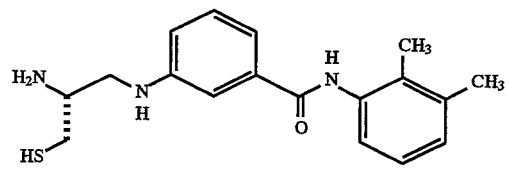

or a pharmaceutically acceptable salt thereof.

9. The compound of claim 7 which is:

3-[2(R)-Amino-3-mercaptopropylamino]-4-methyl-N-(2,3-dimethylphenyl)-benzamide

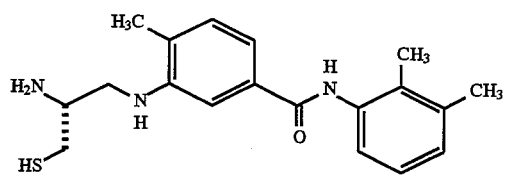

or a pharmaceutically acceptable salt thereof.

10. The compound of claim 7 which is:

4-[2(R)-Amino-3-mercaptopropylamino]-2-(2,3-dimethylphenyl)-isoindolin-1-one or a pharmaceutically acceptable salt thereof.

11. The compound of claim 7 which is:
3-[2(R)-Amino-3-mercaptopropylaminomethyl]-N-(2,3-dimethylphenyl)-benzamide

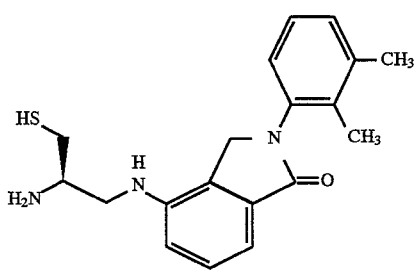

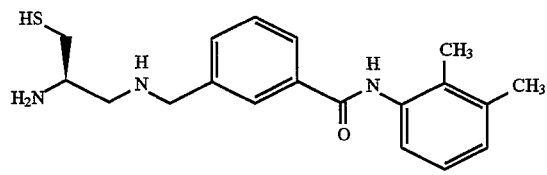

or a pharmaceutically acceptable salt thereof.

12. The compound of claim 7 which is:
N-[(2R)-2-amino-3-mercaptopropyl]amino-3-[2-(3-methylphenyl)-trans-ethenyl]benzene

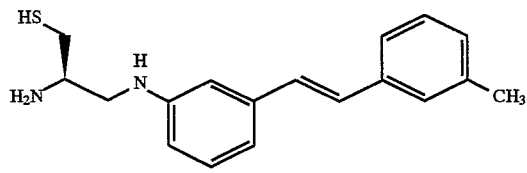

or a pharmaceutically acceptable salt thereof.

13. The compound of claim 7 which is:
N-[(2R)-2-amino-3-mercaptopropyl]amino-3-[(1-naphthylmethyl)oxy]benzene

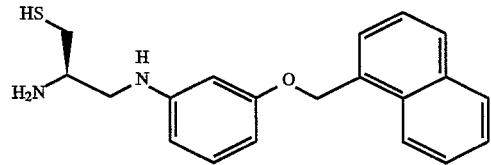

or a pharmaceutically acceptable salt thereof.

14. The compound of claim 7 which is:
N-[(2R)-2-amino-3-mercaptopropyl]amino-4-[(3-(hydroxymethyl)phenyl)oxy]benzene

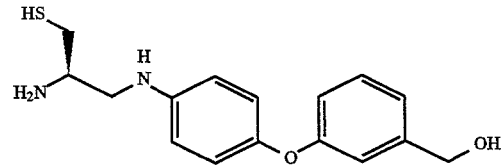

or a pharmaceutically acceptable salt thereof.

15. The compound of claim 7 which is:
N-[(2R)-2-amino-3-mercaptopropyl]amino-2-methyl-4-(phenoxy)benzene

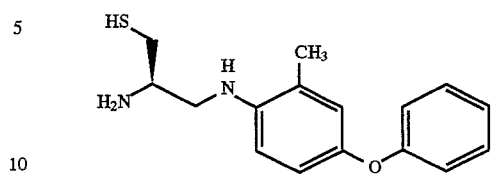

or a pharmaceutically acceptable salt thereof.

16. A pharmaceutical composition comprising a pharmaceutical carrier, and dispersed therein, a therapeutically effective amount of a compound of claim 1.

17. A pharmaceutical composition comprising a pharmaceutical carrier, and dispersed therein, a therapeutically effective amount of a compound of claim 2.

18. A pharmaceutical composition comprising a pharmaceutical carrier, and dispersed therein, a therapeutically effective amount of a compound of claim 3.

19. A pharmaceutical composition comprising a pharmaceutical carrier, and dispersed therein, a therapeutically effective amount of a compound of claim 4.

20. A pharmaceutical composition comprising a pharmaceutical carrier, and dispersed therein, a therapeutically effective amount of a compound of claim 7.

21. A method for inhibiting farnesyl-protein transferase which comprises administering to a mammal in need thereof a therapeutically effective amount of a composition of claim 16.

22. A method for inhibiting farnesyl-protein transferase which comprises administering to a mammal in need thereof a therapeutically effective amount of a composition of claim 17.

23. A method for inhibiting farnesyl-protein transferase which comprises administering to a mammal in need thereof a therapeutically effective amount of a composition of claim 18.

24. A method for inhibiting farnesyl-protein transferase which comprises administering to a mammal in need thereof a therapeutically effective amount of a composition of claim 19.

25. A method for inhibiting farnesyl-protein transferase which comprises administering to a mammal in need thereof a therapeutically effective amount of a composition of claim 20.

26. A method for treating cancer which comprises administering to a mammal in need thereof a therapeutically effective amount of a composition of claim 16.

27. A method for treating cancer which comprises administering to a mammal in need thereof a therapeutically effective amount of a composition of claim 17.

28. A method for treating cancer which comprises administering to a mammal in need thereof a therapeutically effective amount of a composition of claim 18.

29. A method for treating cancer which comprises administering to a mammal in need thereof a therapeutically effective amount of a composition of claim 19.

30. A method for treating cancer which comprises administering to a mammal in need thereof a therapeutically effective amount of a composition of claim 20.

* * * * *